(12) United States Patent
Casey et al.

(10) Patent No.: US 10,980,527 B2
(45) Date of Patent: *Apr. 20, 2021

(54) SYSTEMS AND METHODS FOR PERFORMING SPINE SURGERY

(71) Applicant: NuVasive, Inc., San Diego, CA (US)

(72) Inventors: Niall Casey, Carlsbad, CA (US); James Coleman Lee, San Diego, CA (US); Ali A. Shorooghi, San Diego, CA (US); Gurvinder S. Deol, Raleigh, NC (US); Bradley Alan Heiges, Savannah, GA (US); Nitin Khanna, Chicago, IL (US); Troy B. Woolley, Erie, CO (US)

(73) Assignee: NuVasive, Inc., San Diego, CA (US)

( * ) Notice: Subject to any disclaimer, the term of this patent is extended or adjusted under 35 U.S.C. 154(b) by 143 days.

This patent is subject to a terminal disclaimer.

(21) Appl. No.: 16/160,988

(22) Filed: Oct. 15, 2018

(65) Prior Publication Data

US 2019/0046174 A1  Feb. 14, 2019

Related U.S. Application Data

(63) Continuation of application No. 15/586,059, filed on May 3, 2017, now Pat. No. 10,098,625, which is a
(Continued)

(51) Int. Cl.
*A61B 17/02* (2006.01)
*A61F 2/44* (2006.01)
(Continued)

(52) U.S. Cl.
CPC ........... *A61B 17/025* (2013.01); *A61B 17/02* (2013.01); *A61B 17/0206* (2013.01); *A61B 17/0218* (2013.01); *A61B 17/7032* (2013.01); *A61B 17/863* (2013.01); *A61B 90/30* (2016.02); *A61F 2/30771* (2013.01); *A61F 2/442* (2013.01); *A61F 2/447* (2013.01); *A61F 2/4455* (2013.01); *A61B 2017/00473* (2013.01); *A61B 2017/00477* (2013.01); *A61B 2017/0256* (2013.01);
(Continued)

(58) Field of Classification Search
CPC .......................... A61B 17/0206; A61B 17/025
See application file for complete search history.

(56) References Cited

U.S. PATENT DOCUMENTS

| 186,637 A | 1/1877 | Tanner |
|---|---|---|
| 1,223,812 A | 4/1917 | Listiak |

(Continued)

FOREIGN PATENT DOCUMENTS

| CA | 1142826 | 3/1983 |
|---|---|---|
| CN | 201341901 | 11/2009 |

(Continued)

OTHER PUBLICATIONS

Boucher, H.H., "A Method of Spinal Fusion," The Journal of Bone and Joint Surgery, 1959, vol. 41 B, No. 2, 248-259.

*Primary Examiner* — Andrew Yang

(57) ABSTRACT

This application describes surgical instruments and implants for building a posterior fixation construct across one or more segments of the spinal column during a medialized posterior lumbar interbody fusion (PLIF) procedure.

24 Claims, 15 Drawing Sheets

Related U.S. Application Data continuation of application No. 15/202,464, filed on Jul. 5, 2016, now Pat. No. 9,649,099, which is a continuation of application No. 14/794,709, filed on Jul. 8, 2015, now Pat. No. 9,386,971, which is a continuation of application No. 13/601,986, filed on Aug. 31, 2012, now Pat. No. 9,113,853.

(60) Provisional application No. 61/529,495, filed on Aug. 31, 2011.

(51) Int. Cl.
| | |
|---|---|
| *A61B 17/86* | (2006.01) |
| *A61B 90/30* | (2016.01) |
| *A61B 17/70* | (2006.01) |
| *A61F 2/30* | (2006.01) |
| *A61B 17/00* | (2006.01) |

(52) U.S. Cl.
CPC .......... *A61B 2090/306* (2016.02); *A61F 2002/30593* (2013.01); *A61F 2002/30774* (2013.01); *A61F 2002/30828* (2013.01); *A61F 2002/30904* (2013.01); *A61F 2002/448* (2013.01)

(56) References Cited

U.S. PATENT DOCUMENTS

| | | |
|---|---|---|
| 1,456,116 A | 5/1923 | Bessesen |
| 2,807,259 A | 9/1957 | Guerriero |
| 3,030,948 A | 4/1962 | Loeffler |
| 3,384,077 A | 5/1968 | Gauthier |
| 3,509,873 A | 5/1970 | Karlin |
| 3,522,799 A | 8/1970 | Gauthier |
| 3,724,449 A | 4/1973 | Gauthier |
| 3,749,088 A | 7/1973 | Kohlmann |
| 3,965,890 A | 6/1976 | Gauthier |
| 4,024,859 A | 5/1977 | Slepyan |
| 4,116,232 A | 9/1978 | Rabban |
| 4,151,837 A | 5/1979 | Millard |
| 4,156,424 A | 5/1979 | Burgin |
| 4,165,746 A | 8/1979 | Burgin |
| 4,457,300 A | 7/1984 | Budde |
| 4,461,284 A | 7/1984 | Fackler |
| 4,686,972 A | 8/1987 | Kurland |
| 4,702,230 A | 10/1987 | Pelta |
| 4,747,394 A | 5/1988 | Watanabe |
| 4,747,395 A | 5/1988 | Brief |
| 4,817,587 A | 4/1989 | Janese |
| 4,829,985 A | 5/1989 | Couetil |
| 4,852,552 A | 8/1989 | Chaux |
| 4,881,525 A | 11/1989 | Williams |
| 4,934,352 A | 6/1990 | Sullivan |
| 5,052,373 A | 10/1991 | Michelson |
| 5,468,241 A | 11/1995 | Metz-Stavenhagen |
| 5,512,038 A | 4/1996 | O'Neal |
| D369,860 S | 5/1996 | Koros |
| 5,733,290 A | 3/1998 | McCue |
| 5,772,583 A | 6/1998 | Wright |
| 5,795,291 A | 8/1998 | Koros |
| 5,846,192 A | 12/1998 | Teixido |
| 5,865,730 A | 2/1999 | Fox |
| 5,882,298 A | 3/1999 | Sharratt |
| 5,893,831 A | 4/1999 | Koros |
| 5,902,233 A | 5/1999 | Farley |
| 5,928,139 A | 7/1999 | Koros et al. |
| 5,931,777 A | 8/1999 | Sava |
| 5,944,658 A | 8/1999 | Koros |
| 5,967,974 A | 10/1999 | Nicholas |
| 5,984,865 A | 11/1999 | Farley |
| 5,993,385 A | 11/1999 | Johnston |
| 6,042,540 A | 3/2000 | Johnston |
| 6,042,542 A | 3/2000 | Koros |
| 6,200,263 B1 | 3/2001 | Person |
| 6,206,826 B1 | 3/2001 | Mathews |
| 6,206,828 B1 | 3/2001 | Wright |
| 6,213,941 B1 | 4/2001 | Benetti |
| 6,224,545 B1 | 5/2001 | Cocchia |
| 6,234,961 B1 | 5/2001 | Gray |
| 6,241,729 B1 | 6/2001 | Estes |
| 6,264,396 B1 | 7/2001 | Dobrovolny |
| 6,296,609 B1 | 10/2001 | Brau |
| 6,322,500 B1 | 11/2001 | Sikora |
| 6,340,345 B1 | 1/2002 | Lees |
| 6,416,465 B2 | 7/2002 | Brau |
| 6,506,151 B2 | 1/2003 | Estes |
| 6,524,238 B2 | 2/2003 | Velikaris |
| 6,602,190 B2 | 8/2003 | Dobrovolny |
| 6,648,818 B2 | 11/2003 | Cartier |
| 6,648,896 B2 * | 11/2003 | Overes ............... A61B 17/025 606/102 |
| 6,685,632 B1 | 2/2004 | Hu |
| 6,692,434 B2 | 2/2004 | Ritland |
| 6,733,444 B2 | 5/2004 | Phillips |
| 6,860,850 B2 | 3/2005 | Phillips |
| 6,887,197 B2 | 5/2005 | Phillips |
| 6,887,198 B2 | 5/2005 | Phillips |
| 6,929,606 B2 | 8/2005 | Ritland |
| 6,951,538 B2 | 10/2005 | Ritland |
| 7,001,333 B2 | 2/2006 | Hamel |
| 7,014,609 B2 | 3/2006 | Cartier |
| 7,029,472 B1 | 4/2006 | Fortin |
| 7,056,287 B2 | 6/2006 | Taylor |
| 7,056,321 B2 | 6/2006 | Pagliuca |
| 7,108,698 B2 | 9/2006 | Robbins |
| 7,147,599 B2 | 12/2006 | Phillips |
| 7,166,073 B2 | 1/2007 | Ritland |
| 7,182,729 B2 | 2/2007 | Abdelgany |
| 7,182,731 B2 | 2/2007 | Nguyen |
| 7,207,949 B2 | 4/2007 | Miles et al. |
| 7,207,992 B2 | 4/2007 | Ritland |
| 7,214,186 B2 | 5/2007 | Ritland |
| 7,220,262 B1 | 5/2007 | Hynes |
| 7,235,048 B2 | 6/2007 | Rein |
| 7,235,076 B2 | 6/2007 | Pacheco |
| 7,294,104 B2 | 11/2007 | Person |
| 7,306,603 B2 | 12/2007 | Boehm, Jr. |
| 7,374,534 B2 | 5/2008 | Dalton |
| 7,396,328 B2 | 7/2008 | Penenberg |
| 7,455,639 B2 | 11/2008 | Ritland |
| 7,473,223 B2 | 1/2009 | Fetzer |
| 7,473,269 B1 | 1/2009 | Hynes |
| 7,537,565 B2 | 5/2009 | Bass |
| 7,569,014 B2 | 8/2009 | Bass |
| 7,582,058 B1 | 9/2009 | Miles et al. |
| 7,588,537 B2 | 9/2009 | Bass |
| 7,654,954 B1 | 2/2010 | Phillips |
| 7,691,057 B2 | 4/2010 | Miles et al. |
| 7,699,877 B2 | 4/2010 | Davison |
| 7,722,618 B2 | 5/2010 | Estes |
| 7,744,530 B2 | 6/2010 | Person |
| 7,753,844 B2 | 7/2010 | Sharratt |
| 7,758,501 B2 | 7/2010 | Frasier |
| 7,785,353 B2 | 8/2010 | Sybert |
| 7,819,801 B2 | 10/2010 | Miles et al. |
| 7,824,429 B2 | 11/2010 | Culbert |
| 7,850,608 B2 | 12/2010 | Hamada |
| 7,887,566 B2 | 2/2011 | Hynes |
| 7,905,840 B2 | 3/2011 | Pimenta et al. |
| 7,909,829 B2 | 3/2011 | Patel |
| 7,909,848 B2 | 3/2011 | Patel |
| 7,927,337 B2 | 4/2011 | Keller |
| 7,931,589 B2 | 4/2011 | Cohen |
| 7,935,053 B2 | 5/2011 | Karpowicz |
| 7,946,982 B2 | 5/2011 | Hamada |
| 7,959,564 B2 | 6/2011 | Ritland |
| 7,998,176 B2 | 6/2011 | Culbert |
| 7,981,031 B2 | 7/2011 | Frasier |
| 7,998,175 B2 | 8/2011 | Kim |
| 8,062,217 B2 | 11/2011 | Boucher |
| 8,066,710 B2 | 11/2011 | Estes |
| 8,075,595 B2 | 12/2011 | Kim |
| 8,109,977 B2 | 2/2012 | Culbert |

(56) References Cited

U.S. PATENT DOCUMENTS

| | | |
|---|---|---|
| 8,137,284 B2 | 3/2012 | Miles et al. |
| 8,251,997 B2 | 8/2012 | Michelson |
| 8,313,430 B1 | 11/2012 | Pimenta |
| 8,449,463 B2 | 5/2013 | Nunley et al. |
| 8,636,655 B1 | 1/2014 | Childs |
| 9,486,133 B2 | 11/2016 | Lee et al. |
| 2001/0037123 A1 | 11/2001 | Hancock |
| 2002/0147387 A1 | 10/2002 | Paolitto |
| 2005/0192486 A1 | 9/2005 | Hamel |
| 2005/0240081 A1 | 10/2005 | Eliachar |
| 2005/0277812 A1 | 12/2005 | Myles |
| 2006/0183978 A1 | 8/2006 | Howard |
| 2006/0206009 A1 | 9/2006 | Von Wald |
| 2007/0038033 A1 | 2/2007 | Jones |
| 2007/0073112 A1 | 3/2007 | Holmes |
| 2007/0083086 A1 | 4/2007 | LeVahn |
| 2007/0129608 A1 | 6/2007 | Sandhu |
| 2007/0208228 A1 | 9/2007 | Pavento |
| 2007/0238932 A1 | 10/2007 | Jones |
| 2008/0071145 A1 | 3/2008 | Bjork |
| 2008/0114208 A1 | 5/2008 | Hutton |
| 2008/0146881 A1 | 6/2008 | Alimi |
| 2008/0146885 A1 | 6/2008 | Protopsaltis |
| 2008/0221394 A1 | 9/2008 | Melkent et al. |
| 2008/0249372 A1 | 10/2008 | Reglos |
| 2009/0012370 A1 | 1/2009 | Gutierrez |
| 2009/0012527 A1 | 1/2009 | Mignucci |
| 2009/0036746 A1 | 2/2009 | Blackwell et al. |
| 2009/0076333 A1 | 3/2009 | Bjork |
| 2009/0076516 A1 | 3/2009 | Lowry |
| 2009/0105547 A1 | 4/2009 | Vayser |
| 2009/0124861 A1 | 5/2009 | Fetzer |
| 2009/0227845 A1 | 9/2009 | Lo |
| 2010/0081885 A1 | 4/2010 | Wing |
| 2010/0113885 A1 | 5/2010 | Mcbride |
| 2010/0174146 A1 | 7/2010 | Miles et al. |
| 2010/0217089 A1 | 8/2010 | Farley |
| 2010/0298647 A1 | 11/2010 | Black |
| 2010/0298648 A1 | 11/2010 | Gray |
| 2010/0312068 A1 | 12/2010 | Dalton |
| 2011/0004067 A1 | 1/2011 | Marchek |
| 2011/0034781 A1 | 2/2011 | Loftus |
| 2011/0046448 A1 | 2/2011 | Paolitto et al. |
| 2011/0130793 A1 | 6/2011 | Woolley |
| 2011/0137130 A1 | 6/2011 | Thalgott |
| 2011/0144450 A1 | 6/2011 | Paolitto |
| 2011/0172494 A1 | 7/2011 | Bass |
| 2011/0201897 A1 | 8/2011 | Bertagnoli |
| 2011/0208008 A1 | 8/2011 | Michaeli |
| 2011/0224497 A1 | 9/2011 | Weiman |
| 2011/0245836 A1 | 10/2011 | Hamada |
| 2011/0257487 A1 | 10/2011 | Thalgott |
| 2011/0301423 A1 | 12/2011 | Koros |
| 2012/0083662 A1 | 4/2012 | Hamada |
| 2012/0130180 A1 | 5/2012 | Pell |
| 2012/0172670 A1 | 7/2012 | Hamada |
| 2012/0197300 A1 | 8/2012 | Loftus |
| 2012/0245432 A1 | 9/2012 | Karpowicz |
| 2012/0265021 A1 | 10/2012 | Nottmeier |
| 2012/0330106 A1 | 12/2012 | Wright |
| 2013/0046147 A1 | 2/2013 | Nichter |
| 2013/0123581 A1 | 5/2013 | Fritzinger |
| 2013/0158359 A1 | 6/2013 | Predick |
| 2013/0245383 A1 | 9/2013 | Friedrich |
| 2013/0261401 A1 | 10/2013 | Hawkins |
| 2013/0261402 A1 | 10/2013 | Hawkins |
| 2013/0303859 A1 | 11/2013 | Nowak |
| 2013/0345520 A1 | 12/2013 | Hamada |
| 2014/0024900 A1 | 1/2014 | Capote |
| 2014/0066718 A1 | 3/2014 | Fiechter |
| 2014/0066941 A1 | 3/2014 | Mignucci |
| 2015/0051448 A1 | 2/2015 | Hunt |

FOREIGN PATENT DOCUMENTS

| | | |
|---|---|---|
| CN | 201537102 | 8/2010 |
| DE | 29722605 | 2/1998 |
| EP | 0303773 | 5/1988 |
| EP | 1949860 | 3/2010 |
| EP | 2394584 | 12/2011 |
| FR | 2788958 | 8/2000 |
| GB | 1520832 | 8/1978 |
| JP | 10277043 | 10/1998 |
| WO | WO-199838921 | 9/1998 |
| WO | WO-2004037070 | 5/2004 |
| WO | WO-2004047650 | 6/2004 |
| WO | WO-2007002405 | 1/2007 |
| WO | WO-2010057980 | 5/2010 |
| WO | WO-2011123580 | 10/2011 |
| WO | WO-2012005914 | 1/2012 |
| WO | WO-2012040206 | 3/2012 |
| WO | WO-2012093368 | 7/2012 |
| WO | WO-2012125975 | 9/2012 |
| WO | WO-2013000105 | 1/2013 |
| WO | WO-2013033630 | 3/2013 |
| WO | WO-2013052827 | 4/2013 |

\* cited by examiner

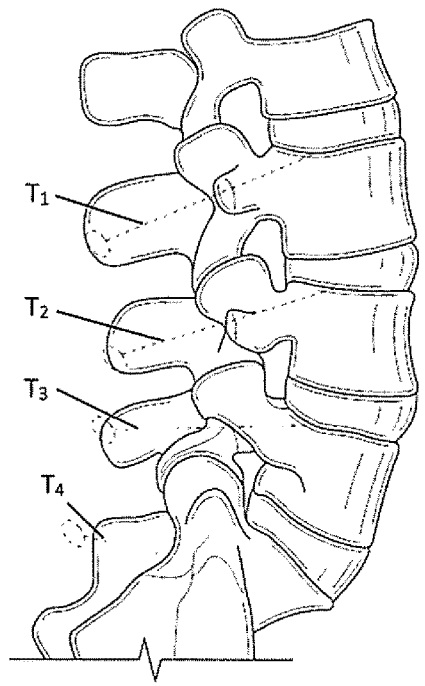
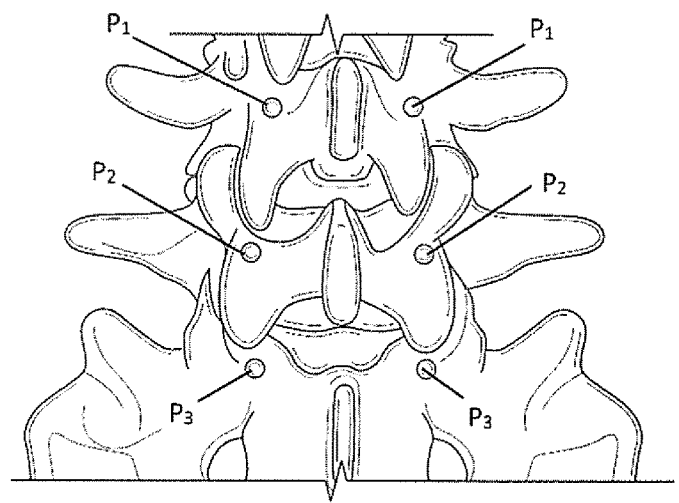
Fig. 41
Fig. 42
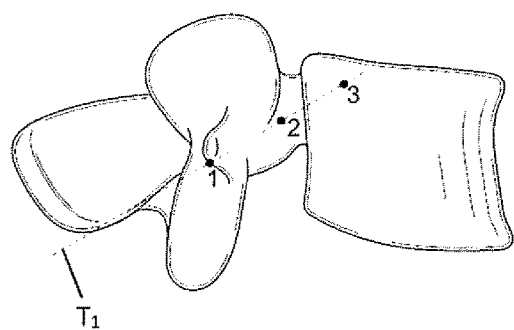
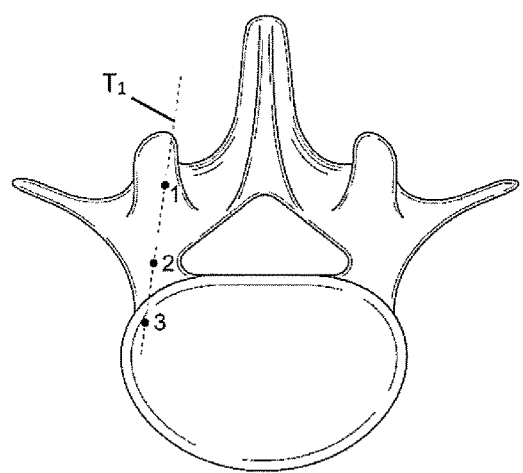
Fig. 43
Fig. 44

SYSTEMS AND METHODS FOR PERFORMING SPINE SURGERY

CROSS-REFERENCES TO RELATED APPLICATIONS

This application is a continuation of U.S. patent application Ser. No. 15/586,059, filed on May 3, 2017, which is a continuation of U.S. patent application Ser. No. 15/202,464, filed on Jul. 5, 2016, now U.S. Pat. No. 9,649,099, which is a continuation of U.S. patent application Ser. No. 14/794,709, filed on Jul. 8, 2015, now U.S. Pat. No. 9,386,971, which is a continuation of U.S. patent application Ser. No. 13/601,986, filed on Aug. 31, 2012, now U.S. Pat. No. 9,113,853, which claims the benefit of priority under 35 U.S.C. 119(e) from U.S. Provisional Patent Application Ser. No. 61/529,495, filed on Aug. 31, 2011, and entitled "Tissue Retraction Assembly and Related Methods," the entire contents of which are each hereby expressly incorporated by reference into this disclosure as if set forth fully herein.

FIELD

This application describes surgical instruments and implants for performing minimally invasive posterior fusion across one or more segments of the spinal column.

BACKGROUND

Posterior Lumbar Interbody Fusion (PLIF) involves access the intervertebral disc space from a posterior approach, removing bone and disc material, and positioning one or more intervertebral implants into the disc space. Additional fixation hardware in the form of pedicle screws and rods are also generally applied to stabilize the spine in position until fusion occurs through the disc space. The pedicle screws are advanced into the vertebral body through the pedicle starting at the intersection of the transverse process and the inferior articulating process of the superior facet. Typical trajectories between pedicle screws within the same vertebral body converge and the trajectory is also often directed inferiorly. Thus, in order to accommodate the implantation of the fixation hardware the traditional PLIF exposure requires exposure out to transverse process which includes stripping of musculature and associated morbidity.

The instruments, tools, and techniques described herein are directed towards reducing the exposure required to perform an instrumented PLIF and other challenges associated with PLIF procedures.

SUMMARY OF THE INVENTION

The present application describes a medialized PLIF exposure. The medialized exposure can be made much smaller than the traditional exposure. Exposure does not require stripping of musculature all the way out to the transverse process. Exposure generally opens out only to the facet joints on the lateral margin. Screws are still advanced into the vertebral body through the pedicle, however, starting point is more medial and slightly inferior. The starting point is typically just medial and inferior to the articulating surface of the superior facet.

The retractor is designed for use during spinal surgery, and particularly for a medialized PLIF (posterior interbody fusion) surgery. The retractor moves and maintains tissue out of the area between the retractor blades to provide access to the spine. The narrow blades may be advanced to the spine first with the use of an attachment handle. The connectors on each side of the retractor may then be attached to the respective connection post on the blades and the handles can be removed. The retractor has a dual translating rack (as opposed to a single arm that moves in relation to a fixed arm). This permits the pressure distribution to be equal on both sides of the access corridor when being opened, such that the center of the access corridor doesn't shift during opening. The retractor body may be attached to an articulating arm (A-arm), which is turn is attached to the bedrail to fix the position of the retractor.

The blades attach to the retractor body at the open receptacles. The engagement latch inside the open receptacle moves freely on its own so that it will be pressed inside the locking arm when the blade is being inserted and will be spring loaded back into locking position once the blade is fully inserted. To release the blade from the retractor, the release button is pressed which will cause the engagement latch to move back into the locking arm so that the blade can slide out. When the release button is released, torsion springs force the release button and engagement latch back into their locked position.

The two-tiered connection post allows the retractor blades to be attached to the retractor body without (or before) removing the attachment handle from the blade, or, one of the blades fixed relative to the table (via an A-arm) prior to attaching the retractor body to the blade. The connection posts of the blades also permit rotation of the blades about the axis of the notch receptacle such that the blades self align and reduce pressure points on the retracted tissue. The connection post is fixed relative to the blade by the connection nut making it so that the blade cannot rotate around the connection post. Instead, the blade rotates via the engagement between the connection post and the locking arm. The open receptacle of the locking arm securely surrounds the lower tier of the connection post, but the connection post is free to rotate inside the open receptacle 360 degrees.

Friction mechanisms are provided to create friction between the pivot piece and the track connector and the pivot piece and locking arm. This prevents the retractor arms from flopping around. A release button is provided on the locking arm of the moving arm so that the blades can be released from the retractor. Pressing the release button will move the engagement latch backwards and the blades can then slide out. When the release button is released, torsion springs force the release button and engagement latch back into their locked position. The engagement latch moves into the arm independent of the release button such that the release button does not move when the blades are inserted.

The thumb tab of the locking mechanism is connected to a pinion shaft so it can be pulled to an upright position. Once in the upright position the thumb tab can be rotated which adjusts the retractor and the operative corridor created by it. This retractor has a dual translating rack so that both arms of the retractor move instead of just one arm. This is advantageous because it prevents slipping of the retractor arm that often occurs with retractors having a fixed arm because of the pressure differences between the two arms. With this retractor, the pressure on both arms is equal so neither arm will slip, providing a more predictable access corridor. The adjustment mechanism includes a pawl so that the racks can only move in one direction at a time. When the desired access has been achieved, the surgeon can rotate the pawl that will lock the thumb tab in place. This is advantageous since it will insure that the thumb tab is not accidently rotated during surgery that would cause the retractor to open up more than necessary. A ball plunger holds the pawl open when one wishes to close the retractor. This prevents the user from having to hold the pawl open while closing the left and right arms.

A bone anchor provided is configured for use with the tissue retractor during a medialized PLIF procedure according to one embodiment. By way of example only, the bone anchor includes a tulip and a shank. The tulip is configured to be coupled to the shank in situ if desired, that is, after the shank has been anchored into the pedicle. The tulip is configured to lockingly receive a spinal rod. The shank comprises a thread configuration tailored to the typical bone pattern along the medialized trajectory followed. By way of example only, the shank comprises three different thread zones.

An interbody implant according to one example embodiment is also described. The interbody implant is designed for bilateral placement along the apophyseal ring at each lateral aspect of the disc space. The implant is also configured to be reversible, that is, a single implant configuration can be utilized as either the left implant or right implant (when positioned bilaterally). The implant is also configured to be inserted via either impaction or insert and rotate techniques.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein:

FIGS. 39-48 illustrate various steps in the minimally invasive PLIF procedure of FIG. 1.

DETAILED DESCRIPTION OF A PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The system and method for performing spine surgery disclosed herein boasts a variety of inventive features and components that warrant patent protection, both individually and in combination.

Figure 1:
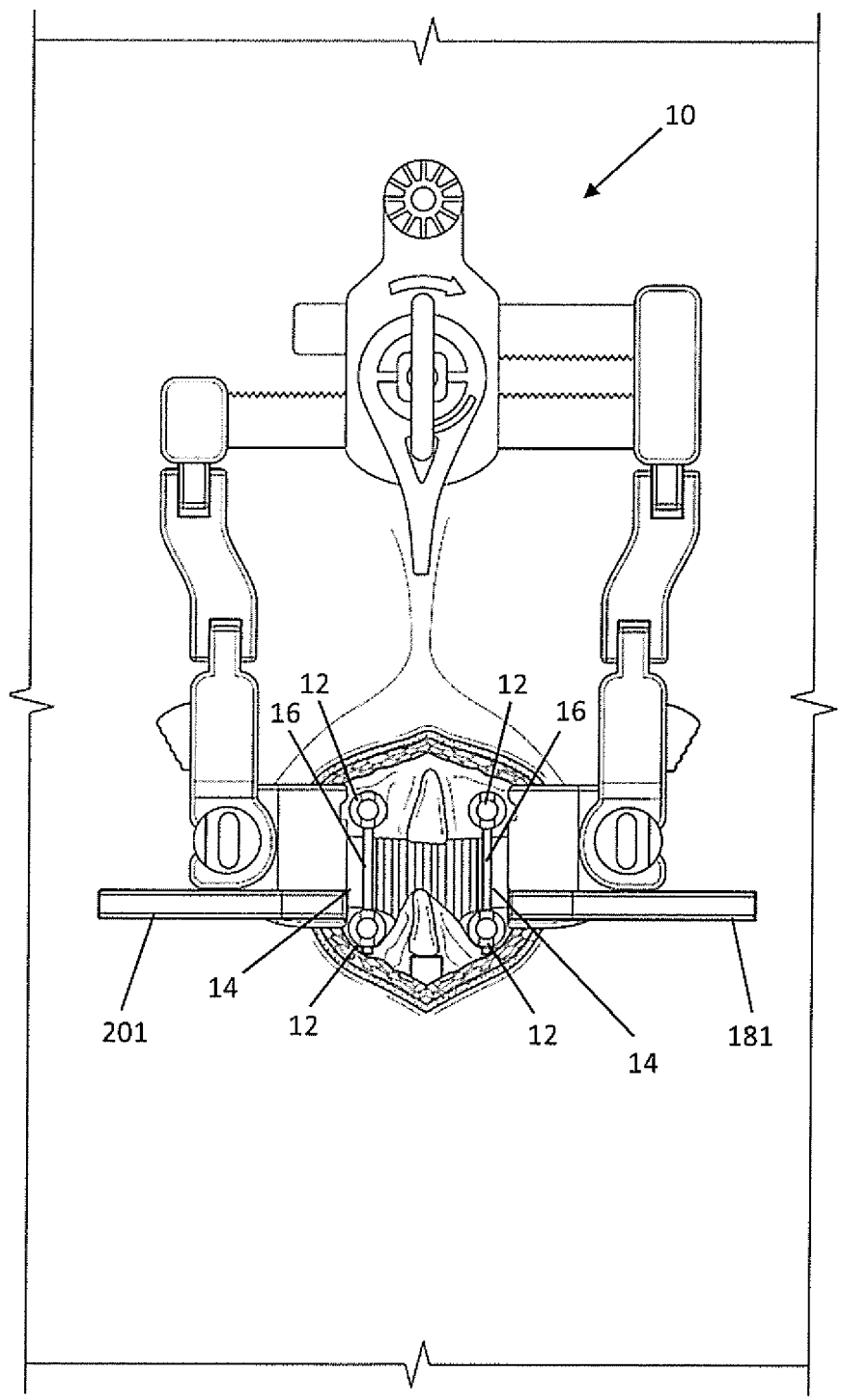
FIG. 1 is a top view of a minimally invasive surgical exposure created by one example of a tissue retraction system in use during a posterior lumbar interbody fusion (PLIF) procedure according to one example embodiment.
Figure 2:
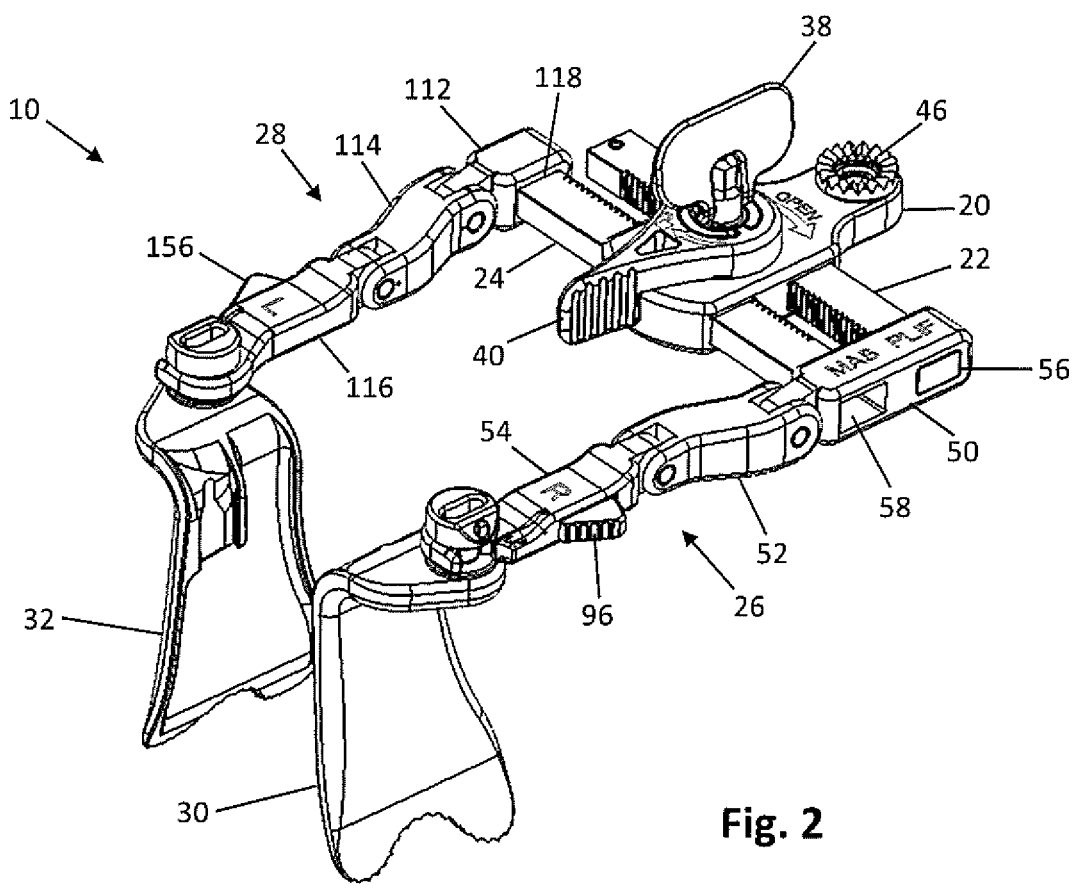
FIGS. 2 and 3 are perspective and side views, respectively, of the tissue retraction system of FIG. 1.
Figure 3:
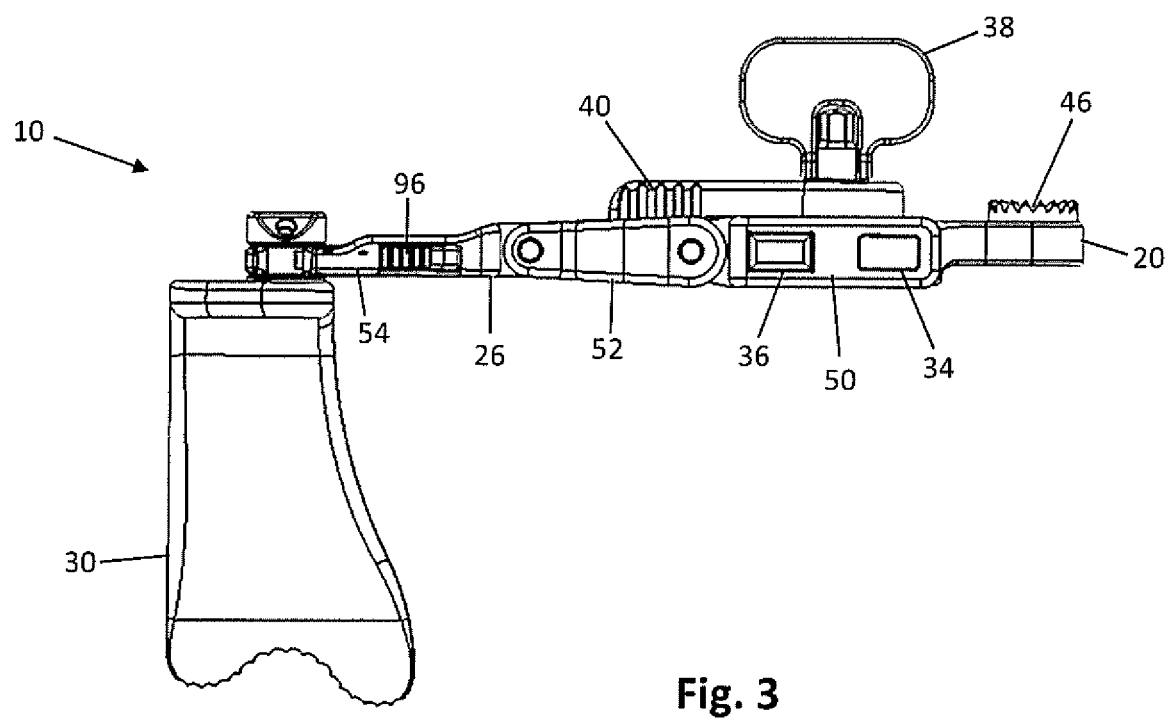
Figure 4:
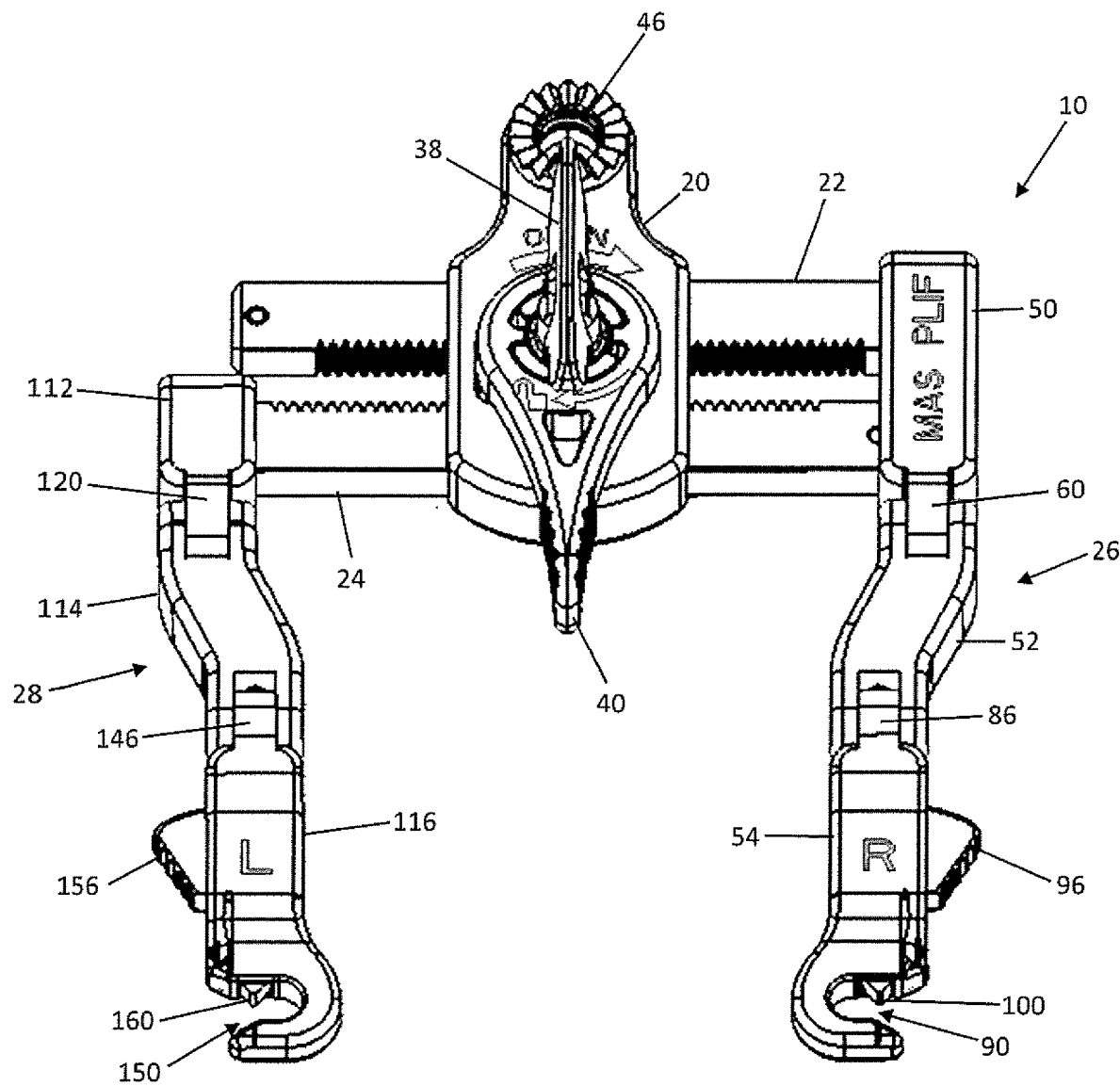
FIG. 4 is a perspective view of the retractor forming part of the tissue retraction system of FIG. 2.
Figure 5:
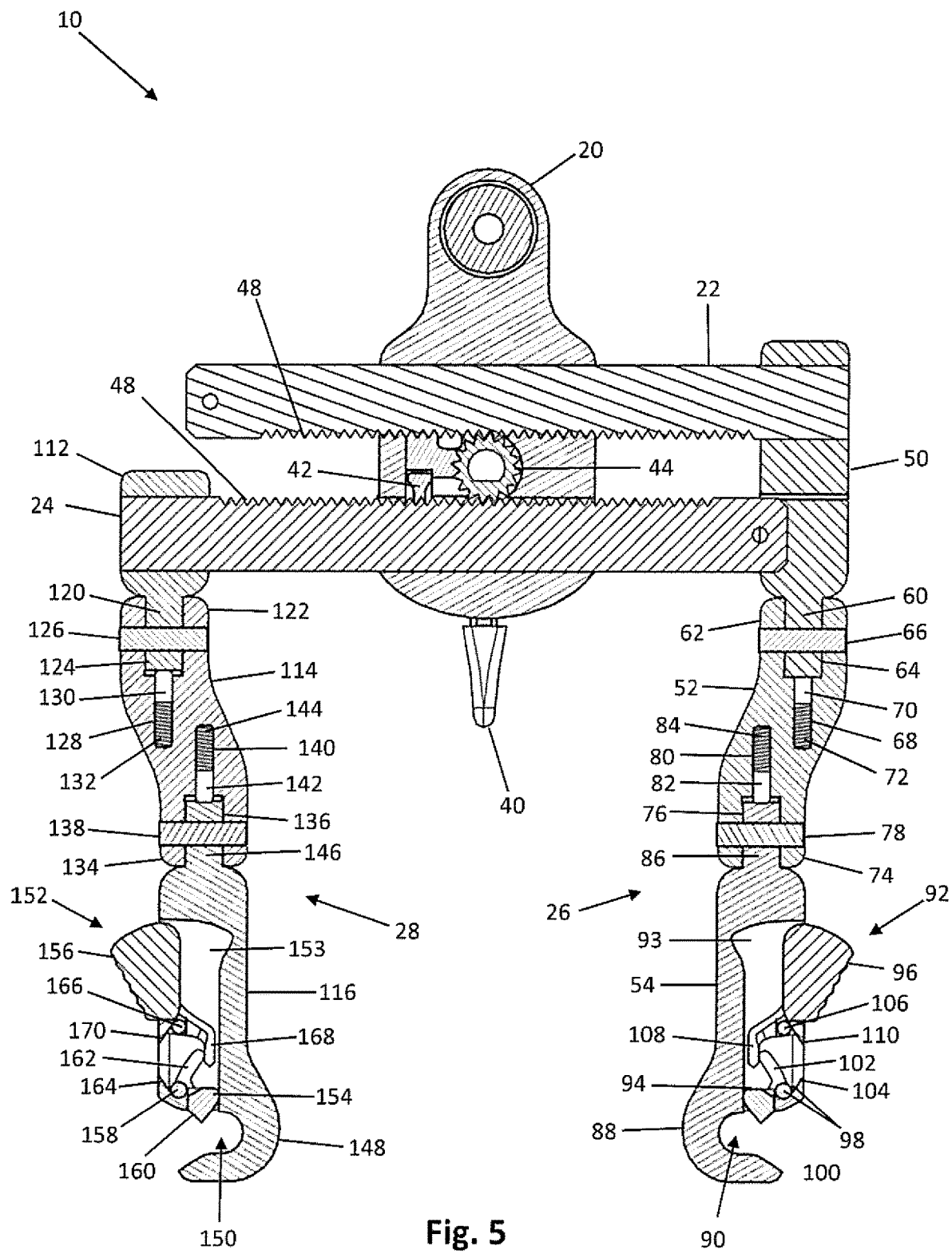
FIG. 5 is a sectional view of the retractor of FIG. 2.
Figure 6:
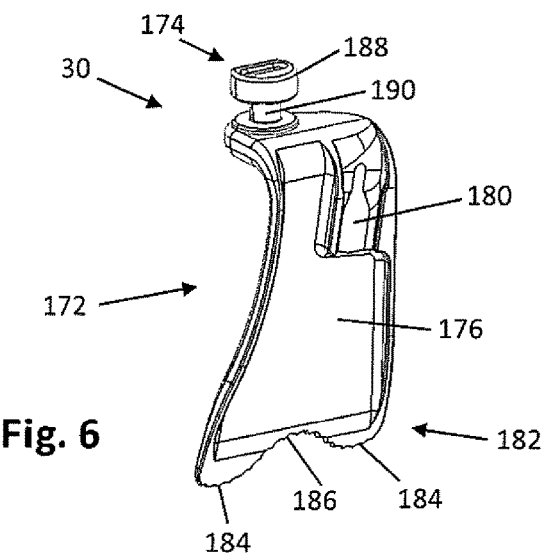
FIGS. 6-11 are various views of a right retractor blade forming part of the tissue retraction system of FIG. 2.
Figure 7:
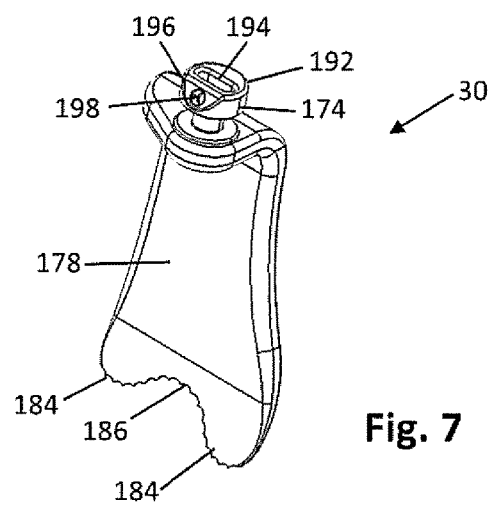
Figure 8:
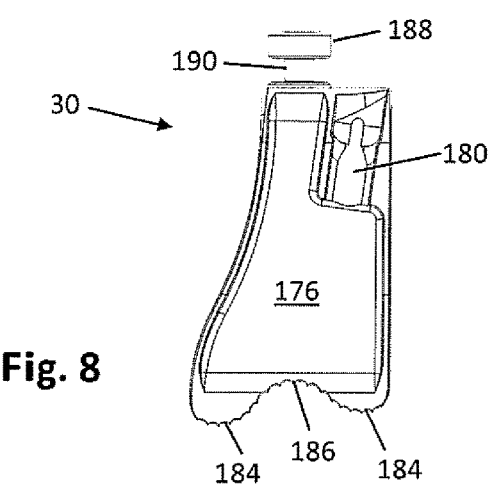
Figure 9:
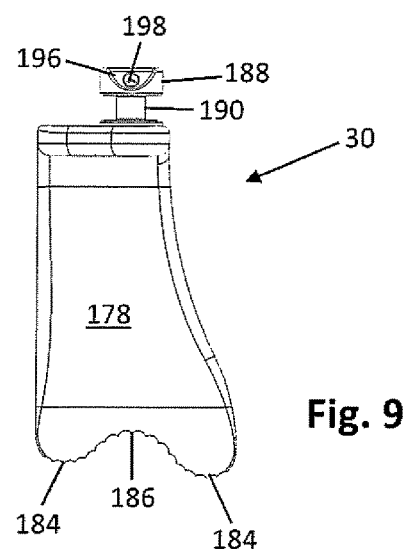

The present application describes a system for performing posterior lumbar interbody fusion (PLIF) surgery. Referring to FIG. 1, the PLIF system includes a tissue retractor 10, a plurality of bone anchors 12, at least one spinal rod 14, and at least one interbody implant 16. The tissue retractor 10 is used to establish and maintain an operative corridor to the surgical target site. Once this access has been established, the bone anchors 12 may be implanted into the vertebral bodies, the disc space and vertebral endplates may be prepared, one or more interbody implants 16 may be inserted into the disc space, and spinal rods 14 may then be used to align and compress the construct.

Referring to FIGS. 2-5, the tissue retractor 10 includes an access driver body 20, first and second racks 22, 24, and right and left arms 26, 28. Right and left retractor blades 30, 32 are removably attached to the right and left arms 26, 28, respectively. In use during a PLIF procedure described herein, it is important that the tissue retractor 10 be positioned relative to the patient such that the access driver body 20 is located above (i.e. cranially of) the wound and in the middle of the patient's back (e.g. directly over the spinal column). This will ensure that the various beneficial features of the tissue retractor 10 described herein are fully utilized. Furthermore, all orientation references herein to "right" and "left" are to be interpreted as relative to the patient. Thus, the right retractor blade 30 will always be positioned within the surgical wound near the patient's right side, and the left retractor blade 32 will always be positioned within the surgical wound near the patient's left side. As will be explained below, this orientation is necessary because the right and left retractor blades are asymmetric in shape and therefore are not interchangeable.

The access driver body 20 has first and second channels 34, 36 extending laterally through the body. The first and second channels 34, 36 are sized and dimensioned to receive the first and second racks 22, 24 respectively therein, and are separated from one another by a distance sufficient to enable placement of a pinion 44 to control translation of the racks 22, 24 as described below. A thumb tab 38 is rotatable to control the directional translation of the racks 22, 24. By way of example only, rotating the thumb tab in a clockwise direction simultaneously causes the first rack 22 to translate toward the right side and the second rack 24 to translate toward the left side. This translation in turn causes the retractor blades 30, 32 to move in the same direction as the racks, controlling the size of the surgical wound. A pawl 40, moveable from a first (e.g. "unlocked") position to a second (e.g. "locked") position is provided to enable locking of the retractor 10 in an open position during use. The pawl 40 includes a wedge 42 (FIG. 5) that is configured to engage the teeth 48 of the second rack 24 and directly prevent translation of the second rack 24 when the pawl 40 is in the second "locked" position. This also indirectly prevents translation of the first rack 22, effectively locking the retractor 10 in an "open" configuration. When the pawl 40 is in the first "unlocked" position, the wedge 42 is disengaged from the teeth 48, allowing free translation of the racks 22, 24. A pinion 44 is positioned between the racks 22, 24 and is mechanically coupled with the thumb tab 38 such that turning the thumb tab 38 causes the pinion 44 to rotate, which in turn causes the racks 22, 24 to translate. The access driver body further includes an articulating arm attachment 46 to enable attachment to an articulating arm during use.

By way of example only, the racks 22, 24 are generally rectangular elongated members having a plurality of teeth 48 distributed on one side of each of the racks 22, 24. The teeth 48 are configured to interact with the pinion 44 described above to allow controlled translation of the arms 26, 28.

The right arm 26 includes a proximal segment 50, a middle segment 52, and a distal segment 54. The proximal segment 50 includes a first aperture 56 and a second aperture 58. The first aperture 56 is configured to fixedly receive the first rack 22 such that the first rack 22 and proximal segment 50 are generally perpendicular to one another. Thus, translation of the first rack 22 in either direction causes a corresponding movement of the right arm 26 in the same direction. The second aperture 58 is configured to slidingly receive the second rack 24 therethrough such that the second rack 24 is able to pass through the proximal segment 50 unencumbered in either direction during translation. The proximal segment 50 further includes a pivot member 60 extending distally from the proximal segment 50, the pivot member 60 configured to be received within a proximal recess 64 formed in the proximal end 62 of the middle segment 52, as described below.

The middle segment 52 is pivotally connected to both the proximal segment 50 and the distal segment 54. The middle segment 52 has a proximal end 62 including a proximal recess 64 configured to receive the pivot member 60 of the proximal segment 50. A pin 66 extends through the proximal end 62 and pivot member 60 and provides an axis about which the middle segment 52 pivots relative to the proximal segment 50. The middle segment 52 further includes a proximal friction recess 68 extending from the proximal recess 64 and configured to house a proximal friction element 70 and spring 72. The proximal friction element 70 and spring 72 interact in such a way that the spring 72 exerts a force on the proximal friction element 70 that in turn exerts a frictional force on the pivot member 60. Thus, the proximal friction element 70 allows movement of the middle segment 52 relative to the proximal segment 50 in the presence of sufficient force to overcome the friction. In the absence of such a force, the proximal friction element 70 operates to maintain the position of the middle segment 52 relative to the proximal segment 50. The middle segment further has a distal end 74 including a distal recess 76 configured to receive the pivot member 86 of the distal segment 54. A pin 78 extends through the distal end 74 and pivot member 86 and provides an axis about which the distal segment 54 pivots relative to the middle segment 52. The middle segment 52 further includes a distal friction recess 80 extending from the distal recess 76 and configured to house a distal friction element 82 and spring 84. The distal friction element 82 and spring 84 interact in such a way that the spring 84 exerts a force on the distal friction element 82 that in turn exerts a frictional force on the pivot member 86. Thus, the distal friction element 82 allows movement of the middle segment 52 relative to the distal segment 54 in the presence of sufficient force to overcome the friction. In the absence of such a force, the distal friction element 82 operates to maintain the position of the middle segment 52 relative to the distal segment 54.

The distal segment 54 is pivotally connected to the middle segment 52 and is configured to releasably engage the right retractor blade 30. The distal segment 54 includes a pivot member 86 extending proximally from the distal segment 54, the pivot member 86 configured to be received within the distal recess 76 formed in the distal end 74 of the middle segment 52, as described above. The distal end 88 of the distal segment 54 includes a receptacle 90 configured to receive the post 190 of the right retractor blade 30. By way of example only, the receptacle 90 is a semi-cylindrical recess that is open on one side. A locking mechanism 92 is provided to releasably lock the right retractor blade 30 within the receptacle 90 during use. The locking mechanism 92 is substantially housed within an inner recess 93. The locking mechanism 92 includes an engagement latch 94 and a release button 96. The engagement latch 94 is held in place by a first pin 98 and includes a blocking element 100 extending into the receptacle 90 and an engagement arm 102 extending away from the blocking element 100. The engagement latch 94 is configured to pivot about the first pin 98. A first torsion spring 104 is provided to bias the engagement latch 94 such that the blocking element 100 protrudes from the inner recess 93 and extends at least partially into the receptacle 90. The release button 96 is held in place by a second pin 106 and includes a release arm 108 extending away from the release button 96. The release button 96 is configured to pivot about the second pin 106. A second torsion spring 110 is provided to bias the release button 96 such that the release button 96 protrudes laterally from the inner recess 93 and is accessible to a user. The locking mechanism 92 is configured in such a way that the engagement arm 102 and release arm 108 are in contact with one another while the locking mechanism 92 is in a resting state.

In use, as the post 190 of the right retractor blade 30 is advanced into the receptacle 90, the post 190 comes into contact with the blocking element 100. As the post 190 continues to advance, the engagement latch 94 pivots about the first pin 98 such that the engagement arm 102 moves away from the release arm 108 and the blocking element 100 retreats into the inner recess 93, allowing the post 190 to pass into the receptacle 90. As the post 190 passes beyond the blocking element 100 and into the receptacle 90, the first torsion spring 104 causes the engagement latch 94 to pivot back into position such that the blocking element 100 again extends into the receptacle 90 and the engagement arm 102 is in contact with the release arm 108. To disengage the right retractor blade 30, the user exerts a pressure on the release button 96, forcing it into the inner recess 93. In the process, the release button 96 pivots about the second pin 106, which causes the release arm 108 to move the engagement arm 102 such that the engagement latch 94 pivots about the first pin 98, which in turn causes the blocking element 100 to retreat into the inner recess 93. With the blocking element 100 removed, the user may disengage the right retractor blade 30 from the right arm 26.

The left arm 28 includes a proximal segment 112, a middle segment 114, and a distal segment 116. The proximal segment 112 includes an aperture 118 configured to fixedly receive the second rack 24 such that the second rack 24 and proximal segment 112 are generally perpendicular to one another. Thus, translation of the second rack 24 in either direction causes a corresponding movement of the left arm 28 in the same direction. The proximal segment 112 further includes a pivot member 120 extending distally from the proximal segment 112, the pivot member 120 configured to be received within a proximal recess 124 formed in the proximal end 122 of the middle segment 114, as described below.

The middle segment 114 is pivotally connected to both the proximal segment 112 and the distal segment 116. The middle segment 114 has a proximal end 122 including a proximal recess 124 configured to receive the pivot member 120 of the proximal segment 112. A pin 126 extends through the proximal end 122 and pivot member 120 and provides an axis about which the middle segment 114 pivots relative to the proximal segment 112. The middle segment 114 further includes a proximal friction recess 128 extending from the proximal recess 124 and configured to house a proximal friction element 130 and spring 132. The proximal friction element 130 and spring 132 interact in such a way that the spring 132 exerts a force on the proximal friction element 130 that in turn exerts a frictional force on the pivot member 120. Thus, the proximal friction element 130 allows movement of the middle segment 114 relative to the proximal segment 112 in the presence of sufficient force to overcome the friction. In the absence of such a force, the proximal friction element 130 operates to maintain the position of the middle segment 114 relative to the proximal segment 112. The middle segment 114 further has a distal end 134 including a distal recess 136 configured to receive the pivot member 146 of the distal segment 116. A pin 138 extends through the distal end 134 and pivot member 146 and provides an axis about which the distal segment 116 pivots relative to the middle segment 114. The middle segment 114 further includes a distal friction recess 140 extending from the distal recess 136 and configured to house a distal friction element 142 and spring 144. The distal friction element 142 and spring 144 interact in such a way that the spring 144 exerts a force on the distal friction element 142 that in turn exerts a frictional force on the pivot member 146. Thus, the distal friction element 142 allows movement of the middle segment 114 relative to the distal segment 116 in the presence of sufficient force to overcome the friction. In the absence of such a force, the distal friction element 142 operates to maintain the position of the middle segment 114 relative to the distal segment 116.

The distal segment 116 is pivotally connected to the middle segment 114 and is configured to releasably engage the left retractor blade 32. The distal segment 116 includes a pivot member 146 extending proximally from the distal segment 116, the pivot member 146 configured to be received within the distal recess 136 formed in the distal end 134 of the middle segment 114, as described above. The distal end 148 of the distal segment 116 includes a receptacle 150 configured to receive the post 218 of the left retractor blade 32. By way of example only, the receptacle 150 is a semi-cylindrical recess that is open on one side. A locking mechanism 152 is provided to releasably lock the left retractor blade 32 within the receptacle 150 during use. The locking mechanism 152 is substantially housed within an inner recess 153. The locking mechanism 152 includes an engagement latch 154 and a release button 156. The engagement latch 154 is held in place by a first pin 158 and includes a blocking element 160 extending into the receptacle 150 and an engagement arm 162 extending away from the blocking element 160. The engagement latch 154 is configured to pivot about the first pin 158. A first torsion spring 164 is provided to bias the engagement latch 154 such that the blocking element 160 protrudes from the inner recess 153 and extends at least partially into the receptacle 150. The release button 156 is held in place by a second pin 166 and includes a release arm 168 extending away from the release button 156. The release button 156 is configured to pivot about the second pin 166. A second torsion spring 170 is provided to bias the release button 156 such that the release button 156 protrudes laterally from the inner recess 153 and is accessible to a user. The locking mechanism 152 is configured in such a way that the engagement arm 162 and release arm 168 are in contact with one another while the locking mechanism 152 is in a resting state.

In use, as the post 218 of the left retractor blade 32 is advanced into the receptacle 150, the post 218 comes into contact with the blocking element 160. As the post 218 continues to advance, the engagement latch 154 pivots about the first pin 158 such that the engagement arm 162 moves away from the release arm 168 and the blocking element 160 retreats into the inner recess 153, allowing the post 218 to pass into the receptacle 150. As the post 218 passes beyond the blocking element 160 and into the receptacle 150, the first torsion spring 164 causes the engagement latch 154 to pivot back into position such that the blocking element 160 again extends into the receptacle 150 and the engagement arm 162 is in contact with the release arm 168. To disengage the left retractor blade 32, the user exerts a pressure on the release button 156, forcing it into the inner recess 153. In the process, the release button 156 pivots about the second pin 166, which causes the release arm 168 to move the engagement arm 162 such that the engagement latch 154 pivots about the first pin 158, which in turn causes the blocking element 160 to retreat into the inner recess 153. With the blocking element 160 removed, the user may disengage the left retractor blade 32 from the left arm 28.

Figure 10:
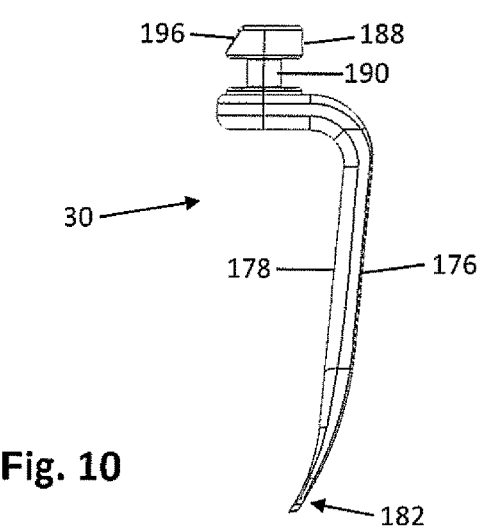
Figure 11:
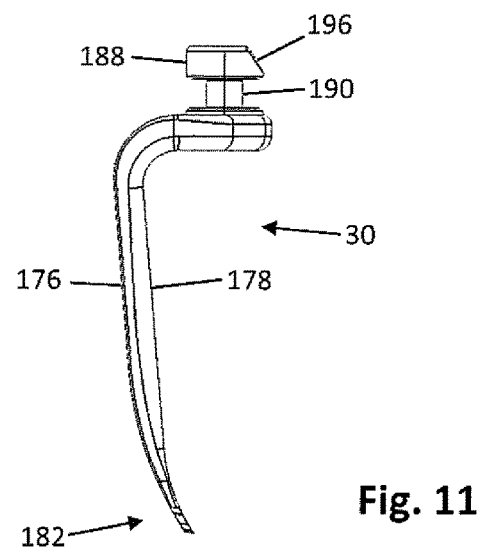
Figure 12:
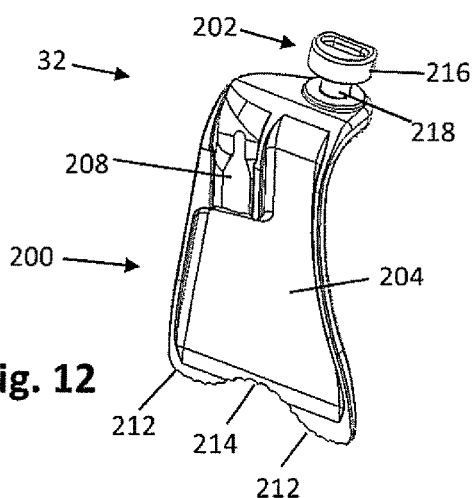
FIGS. 12-17 are various views of a left retractor blade forming part of the tissue retraction system of FIG. 2.
Figure 13:
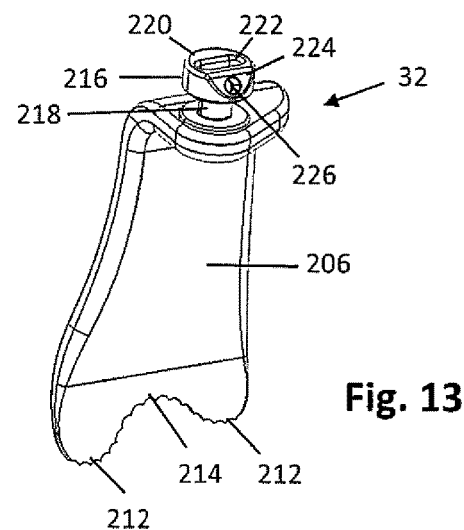
Figure 14:
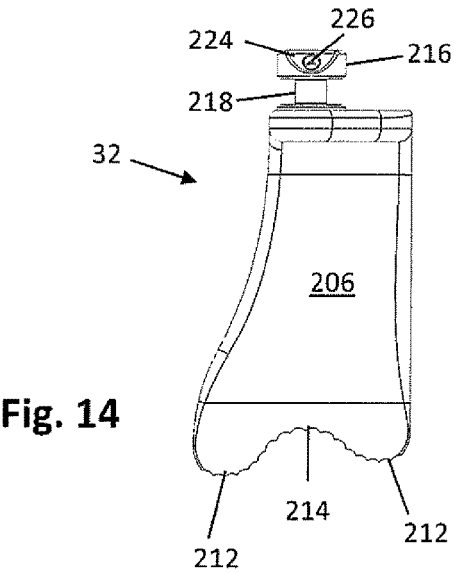
Figure 15:
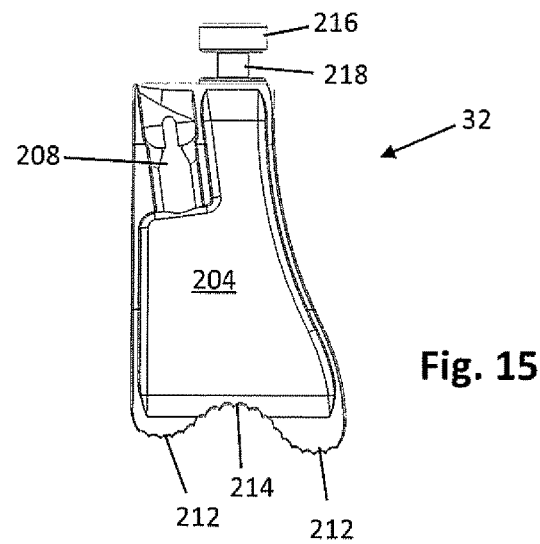

FIGS. 6-11 illustrate an example of a right retractor blade 30 configured for use with the tissue retractor 10 described above, according to one embodiment. The right retractor blade 30 has a blade portion 172 and a connector 174. The blade portion 172 has an interior face 176 and an exterior face 178. The exterior face 178 is generally smooth and rests against the soft tissue during use. The retractor blade 30 is configured to rotate such that the blade 30 can self-align against the tissue, or in other words, find the best natural position against the tissue in order to reduce pressure points. The interior face 176 includes a light guide 180. The light source 181 (FIG. 1) slides down the light guide 180 to illuminate the surgical target site. The light source 181 may be a bundle of fiber optic cable designed to engage the light guide 180. The light source 181 may also be bendable such that it can be bent out of the surgeon's way as it exits the operative corridor. The light source 181 may be engaged to the retractor blade 30 prior to inserting the blade 30. The distal end 182 of the right retractor blade 30 may be angled away from the interior face 176 as shown in FIGS. 10 and 11 or be oriented in a straight in line with the rest of the blade 30. The distal end 182 may be smooth or toothed (as shown by way of example in FIGS. 6-11). The distal end 182 of the blade 30 may also have two outer lobes 184 with a center recess 186 between the outer lobes 184. This configuration allows the right retractor blade 30 to better conform to the patient's bone structure.

The right retractor blade 30 includes a connector 174 for connecting the blade 30 to the right arm 26. The connector 174 has a head 188 and a post 190. The head 188 includes a top surface 192, a recess 194 formed within the top surface 192, a beveled surface 196, and an aperture 198 formed within the beveled surface 196. The recess 194 is generally oblong in shape and is configured to receive the engagement post 272 on the engagement head 266 of the attachment handle 260. The beveled surface 196 is configured to abut against the engagement head 266 of the attachment handle 260, and the aperture 198 is configured to receive the distal tip 276 of the inner shaft 274 of the attachment handle 260, described in further detail in relation to FIGS. 24-27. The head 188 and post 190 are each configured to allow connection of the blade 30 to two instruments at the same time (for example an attachment handle 260 and right arm 26, or attachment handle 260 and articulating arm). This simplifies insertion of the retractor blade 30. It also allows the surgeon to manually retract and position the blade 30 precisely, adjust the access driver body 20 to match the blade(s), and thereafter attach the access driver body 20 to hold the blade(s) in position. According to a preferred usage, for example, the right retractor blade 30 is attached to the attachment handle 260 via the head 188 and advanced to the surgical site. The right retractor blade 30 is retracted into the desired position and then the right arm 26 is connected to the post 190 as described above. The right arm 26 is locked, fixing the position of the blade 30 (it is also possible to insert the blade 30 having the right arm 26 attached to the blade 30, adjust the position of the blade, and then lock the right arm 26 to hold the blade 30 in the desired position prior to attaching the retractor body). The attachment handle 260 is then removed from the head 188.

The right retractor blade 30 is designed to rotate within the receptacle 90 in order to self align in the best possible position against the patient's soft tissue. The connector 174 is fixed relative to the blade 30. The ability for the blade 30 to rotate relative to the retractor 10 derives from the connection between the post 190 and the receptacle 90 of the right arm 26. The post 190 can rotate freely 360 degrees within the receptacle 90.

Figure 16:
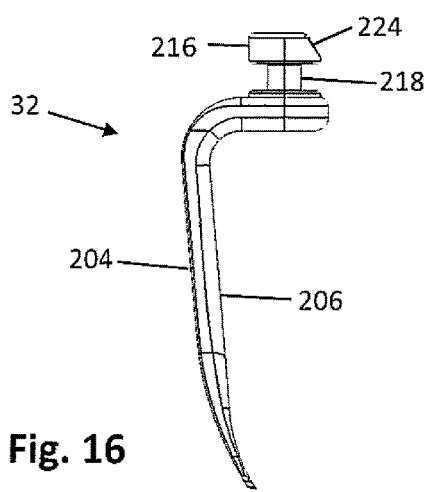
Figure 17:
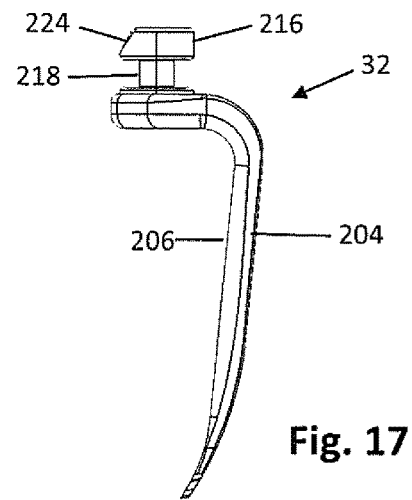
Figure 18:
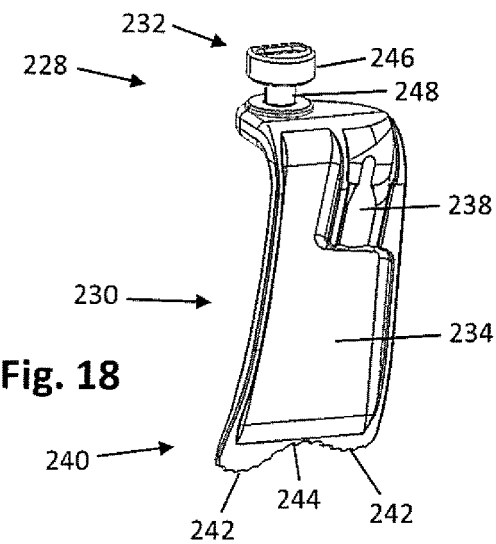
FIGS. 18-23 are various views of a narrow left retractor blade forming part of the tissue retraction system of FIG. 2.
Figure 19:
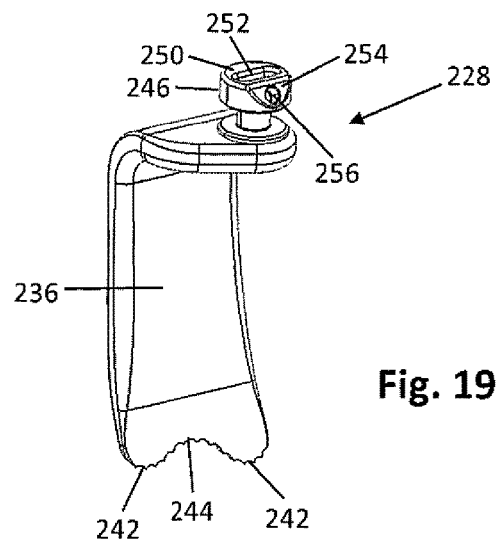
Figure 20:
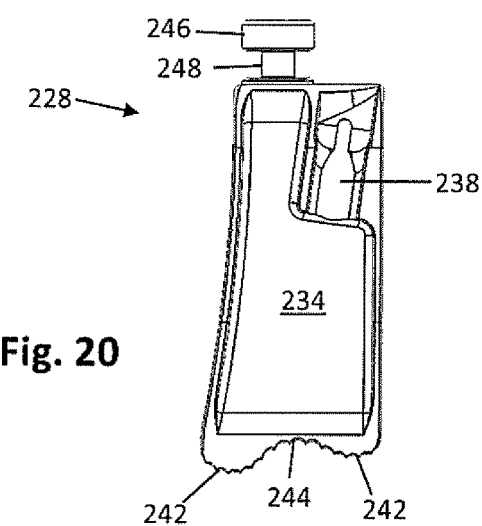
Figure 21:
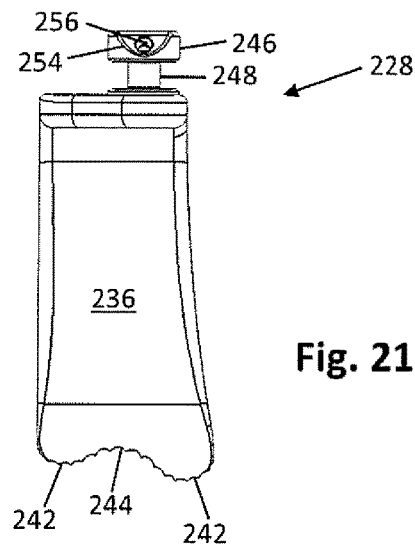

FIGS. 12-17 illustrate an example of a left retractor blade 32 configured for use with the tissue retractor 10 described above, according to one embodiment. The left retractor blade 32 has a blade portion 216 and a connector 218. The blade portion 216 has an interior face 212 and an exterior face 214. The exterior face 214 is generally smooth and rests against the soft tissue during use. The left retractor blade 32 is configured to rotate such that the blade 32 can self-align against the tissue, or in other words, find the best natural position against the tissue in order to reduce pressure points. The interior face 212 includes a light guide 216. The light source 201 (FIG. 1) slides down the light guide 216 to illuminate the surgical target site. The light source 201 may be a bundle of fiber optic cable designed to engage the light guide 216. The light source 201 may also be bendable such that it can be bent out of the surgeon's way as it exits the operative corridor. The light source 201 may be engaged to the retractor blade 32 prior to inserting the blade 32. The distal end 218 of the left retractor blade 32 may be angled away from the interior face 212 as shown in FIGS. 16 and 17 or be oriented in a straight in line with the rest of the blade 32. The distal end 218 may be smooth or toothed (as shown by way of example in FIGS. 12-17). The distal end 218 of the blade 32 may also have two outer lobes 212 with a center recess 214 between the outer lobes 212. This configuration allows the left retractor blade 32 to better conform to the patient's bone structure.

The left retractor blade 32 includes a connector 218 for connecting the blade 32 to the left arm 28. The connector 218 has a head 216 and a post 218. The head 216 includes a top surface 220, a recess 222 formed within the top surface 220, a beveled surface 224, and an aperture 226 formed within the beveled surface 224. The recess 222 is generally oblong in shape and is configured to receive the engagement post 272 on the engagement head 266 of the attachment handle 260. The beveled surface 224 is configured to abut against the engagement head 266 of the attachment handle 260, and the aperture 226 is configured to receive the distal tip 276 of the inner shaft 274 of the attachment handle 260, described in further detail in relation to FIGS. 24-27. The head 188 and post 190 are each configured to allow each of which are configured to allow connection of the blade 32 to two instruments at the same time (for example an attachment handle 260 and left arm 28, or attachment handle 260 and articulating arm). This simplifies insertion of the retractor blade 32. It also allows the surgeon to manually retract and position the blade 32 precisely, adjust the access driver body 20 to match the blade(s), and thereafter attach the access driver body 20 to hold the blade(s) in position. According to a preferred usage, for example, the left retractor blade 32 is attached to the attachment handle 260 via the head 216 and advanced to the surgical site. The left retractor blade 32 is retracted into the desired position and then the left arm 28 is connected to the post 218 as described above. The left arm 28 is locked, fixing the position of the blade 32 (it is also possible to insert the blade 32 having the left arm 28 attached to the blade 32, adjust the position of the blade, and then lock the left arm 28 to hold the blade 32 in the desired position prior to attaching the retractor body). The attachment handle 260 is then removed from the head 216.

The left retractor blade 32 is designed to rotate within the receptacle 150 in order to self align in the best possible position against the patient's soft tissue. The connector 218 is fixed relative to the blade 32. The ability for the blade 32 to rotate relative to the retractor 10 derives from the connection between the post 218 and the receptacle 150 of the left arm 28. The post 218 can rotate freely 360 degrees within the receptacle 150.

As can be appreciated in the figures, the right and left retractor blades 30, 32 each have an asymmetric shape and are therefore not interchangeable, although for example they may be mirror images of one another. The asymmetric shape is advantageous in that it allows for greater conformity to the patient's anatomical structures while also improving the surgical exposure, creating more space and less tissue creep for the surgeon.

FIGS. 18-23 illustrate an example of a narrow right retractor blade 228 configured for use with the tissue retractor 10 described above, according to one embodiment. Although shown and described by way of example in relation to a right blade 228 only, it should be understood that a narrow left retractor blade may be provided in a similar manner without departing from the scope of the disclosure. The narrow right retractor blade 228 may be used as an initial blade to establish the minimally invasive operative corridor to the surgical target site. Once the corridor has been established, the narrow right retractor blade 228 may be disengaged from the right arm 26 and replaced with a right blade 30. The right blade 30 (and left blade 32) has a wider distal portion to help keep more tissue from invading the operative corridor.

Figure 22:
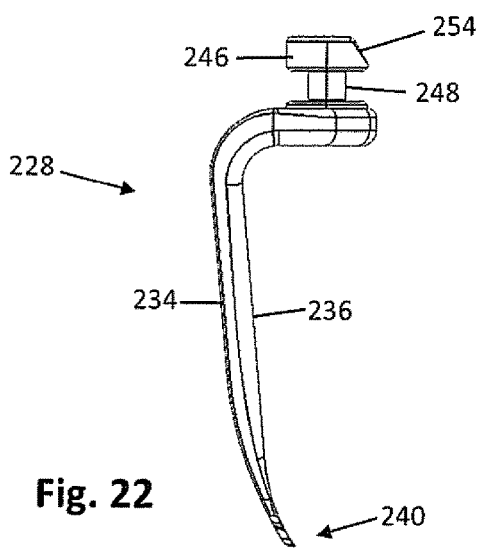
Figure 23:
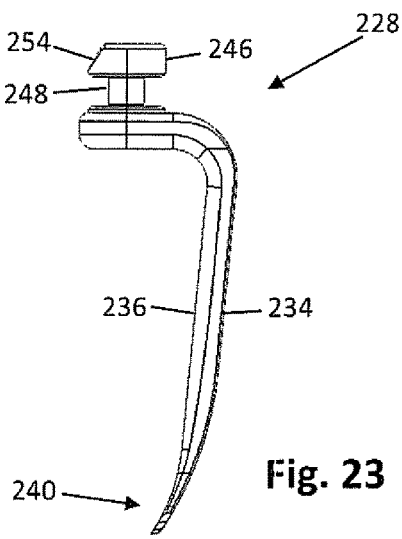
Figure 24:
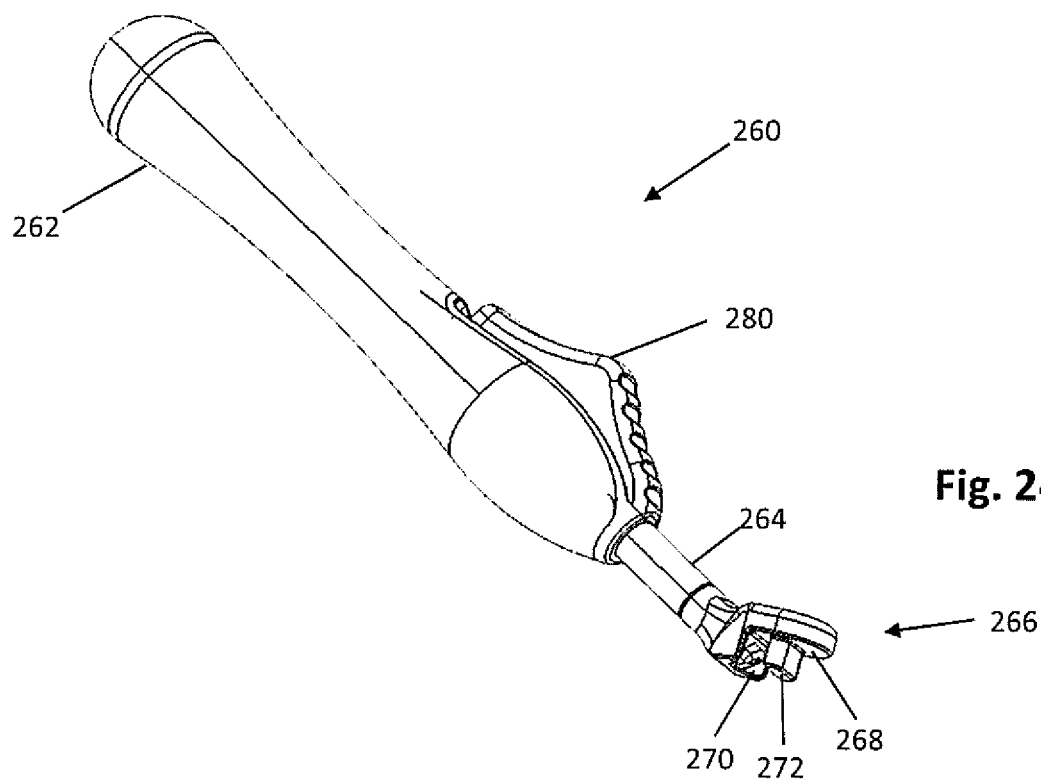
FIG. 24 is a perspective view of one example of a blade holder forming part of the tissue retraction system of FIG. 2.
Figure 25:
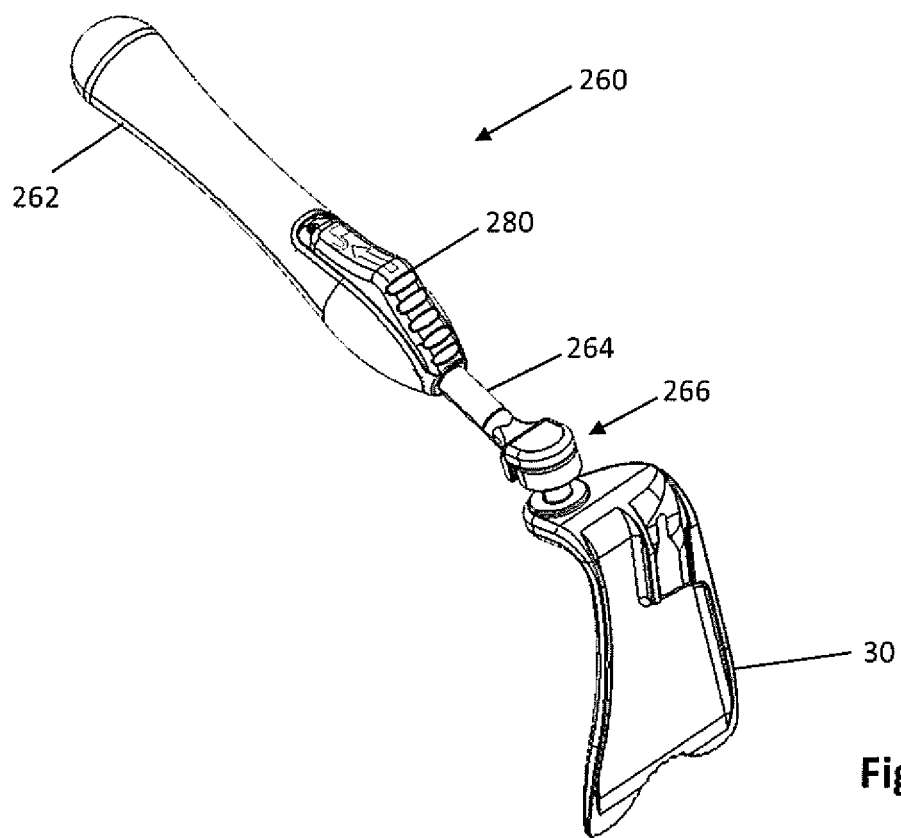
FIGS. 25 and 26 are perspective and side views, respectively, of the blade holder of FIG. 24 coupled with the right retractor blade of FIG. 6.
Figure 26:
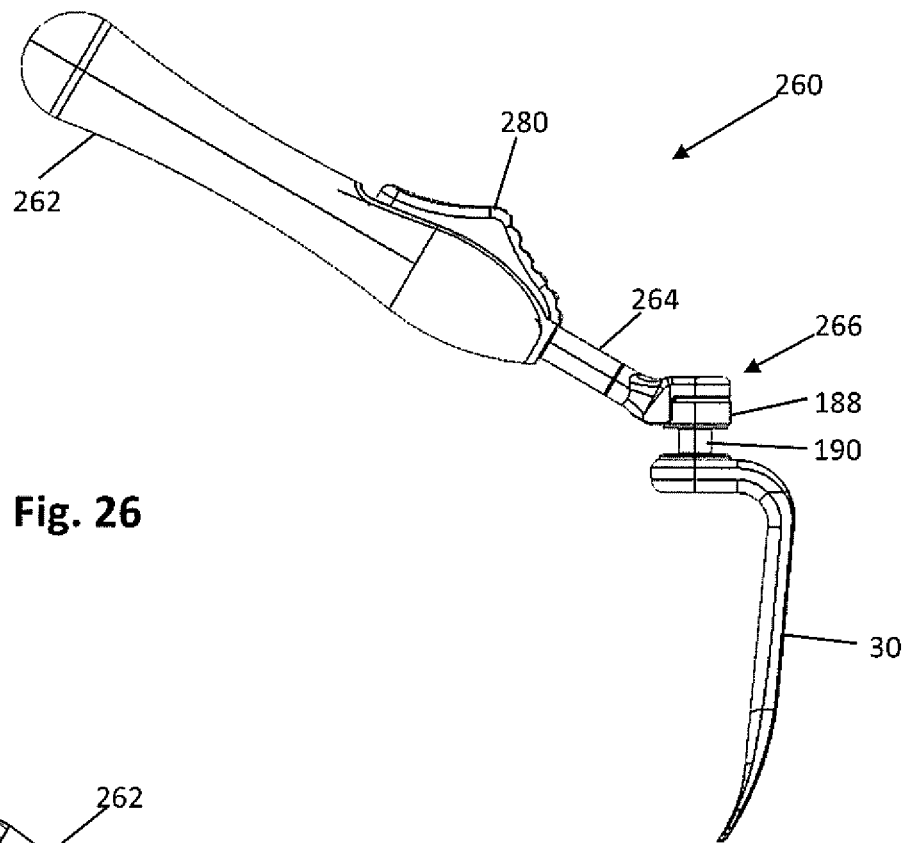
Figure 27:
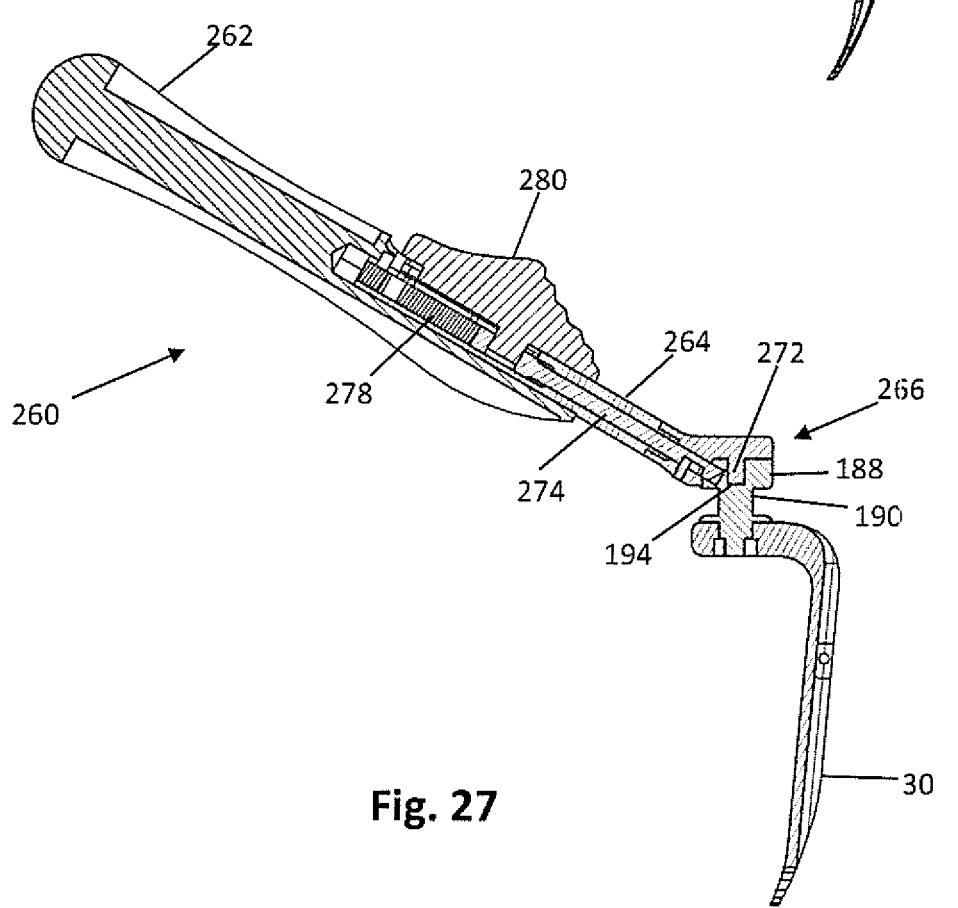
FIG. 27 is a side sectional view of the blade holder and right retractor blade combination of FIG. 25.

The narrow right retractor blade 228 has a blade portion 230 and a connector 232. The blade portion 230 has an interior face 234 and an exterior face 236. The exterior face 236 is generally smooth and rests against the soft tissue during use. The narrow right retractor blade 228 is configured to rotate such that the blade 228 can self-align against the tissue, or in other words, find the best natural position against the tissue in order to reduce pressure points. The interior face 234 includes a light guide 238. The light source (not shown) slides down the light guide 238 to illuminate the surgical target site. The light source may be a bundle of fiber optic cable designed to engage the light guide 238. The light source may also be bendable such that it can be bent out of the surgeon's way as it exits the operative corridor. The light source may be engaged to the narrow right retractor blade 228 prior to inserting the blade 228. The distal end 240 of the narrow right retractor blade 228 may be angled away from the interior face 234 as shown in FIGS. 22 and 23 or be oriented in a straight in line with the rest of the blade 228. The distal end 240 may be smooth or toothed (as shown by way of example in FIGS. 18-23). The distal end 240 of the blade 228 may also have two outer lobes 242 with a center recess 244 between the outer lobes 242. This configuration allows the narrow right retractor blade 228 to better conform to the patient's bone structure.

The narrow right retractor blade 228 includes a connector 232 for connecting the blade 228 to the right arm 26. The connector 232 has a head 246 and a post 248. The head 246 includes a top surface 250, a recess 252 formed within the top surface 250, a beveled surface 254, and an aperture 256 formed within the beveled surface 254. The recess 252 is generally oblong in shape and is configured to receive the engagement post 272 on the engagement head 266 of the attachment handle 260. The beveled surface 254 is configured to abut against the engagement head 266 of the attachment handle 260, and the aperture 256 is configured to receive the distal tip 276 of the inner shaft 274 of the attachment handle 260, described in further detail in relation to FIGS. 24-27. The head 246 and post 248 are each configured to allow connection of the blade 228 to two instruments at the same time (for example an attachment handle 260 and right arm 26, or attachment handle 260 and articulating arm). This simplifies insertion of the retractor blade 228. It also allows the surgeon to manually retract and position the blade 228 precisely, adjust the access driver body 20 to match the blade(s), and thereafter attach the access driver body 20 to hold the blade(s) in position. According to a preferred usage, for example, the narrow right retractor blade 228 is attached to the attachment handle 260 via the head 246 and advanced to the surgical site. The narrow right retractor blade 228 is retracted into the desired position and then the right arm 26 is connected to the post 248 as described above. The right arm 26 is locked, fixing the position of the blade 228 (it is also possible to insert the blade 228 having the right arm 26 attached to the blade 228, adjust the position of the blade, and then lock the right arm 26 to hold the blade 228 in the desired position prior to attaching the retractor body). The attachment handle 260 is then removed from the head 246.

The narrow right retractor blade 228 is designed to rotate within the receptacle 90 in order to self align in the best possible position against the patient's soft tissue. The connector 232 is fixed relative to the blade 228. The ability for the blade 228 to rotate relative to the retractor 10 derives from the connection between the post 248 and the receptacle 90 of the right arm 26. The post 248 can rotate freely 360 degrees within the receptacle 90.

FIGS. 24-27 illustrate one example of an attachment handle 260 configured for use with the tissue retractor 10 described above, according to one embodiment. The attachment handle 260 is shown by way of example (FIGS. 25-27) as engaged with a right retractor blade 30 however the attachment handle 260 may be engaged with any of the retractor blades shown and described herein. The attachment handle 260 includes a grip 262, an elongated outer shaft 264, and an engagement head 266 positioned at the distal end of the outer shaft 264. The engagement head 266 includes a first abutment surface 268 and a second abutment surface 270. A generally oblong engagement post 272 extends generally perpendicularly from the first abutment surface 268. An inner shaft 274 extends through the outer shaft and has a distal tip 276 that is configured to couple with the aperture 198 of the blade 30. The attachment handle 260 further includes a spring 278 that exerts a force on the inner shaft 274 to bias the inner shaft 274 in a distal direction. The proximal end of the inner shaft 274 is attached to a release button 280.

When the attachment handle is coupled with the blade 30, the first abutment surface 268 abuts the top surface 192 of the head 188 of the blade 30. The second abutment surface 270 abuts the beveled surface 196 of the blade 30. The engagement post 272 is inserted into the recess 194 of the blade 30, and the distal tip 276 of the inner shaft 274 is received within the aperture 198 of the blade 30. The distal biasing of the inner shaft 274 keeps the distal tip 276 engaged with the aperture 198 of the blade 30, effectively locking the attachment handle 260 to the blade 30. To disengage, the use pulls back on the release button, which pulls the distal tip 276 of the inner shaft 274 out of the aperture 198 and allows for decoupling of the blade 30 and attachment handle 260.

The various features described herein provide functional benefits during spine surgery. For example, the dual pivots enable adjustment of the arms 26, 28 such that the height of the distal segments may be adjusted while allowing the distal segments to remain parallel to the patient's body. Thus the angle of the retractor blades will remain relatively constant. The friction elements described herein operate to easily allow this adjustment to occur, but also to maintain the desired adjustment without requiring additional hands, tools, or time. The locking element is operable to allow a snap-fit engagement between the retractor blades and the retractor arms without any other manipulation required by the user. Furthermore, the locking element is disengaged by depressing a single button allowing for the removal of the retractor blades.

Figure 28:
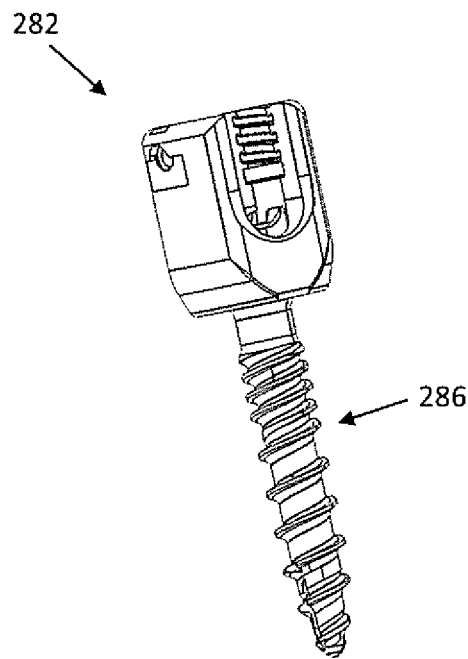
FIGS. 28 and 29 are perspective and exploded perspective views, respectively, of an example of a bone screw suitable for use in the PLIF procedure of FIG. 1.
Figure 29:
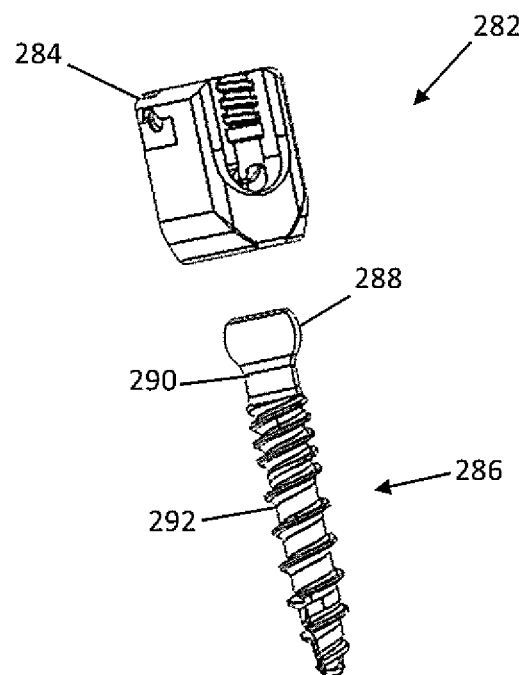
Figure 30:
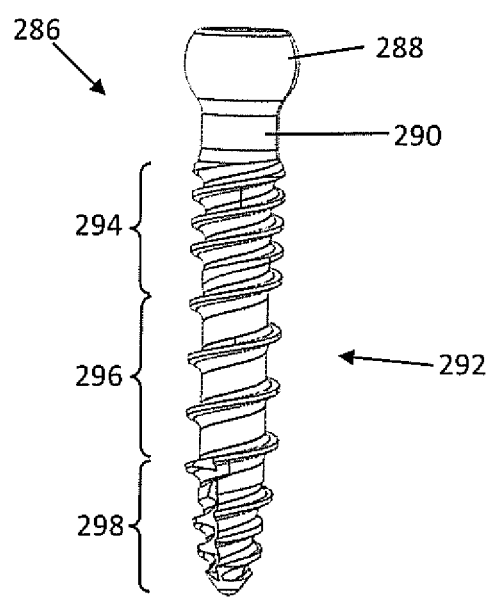
FIG. 30 is a side view of a screw shank forming part of the bone screw of FIG. 28.
Figure 31:
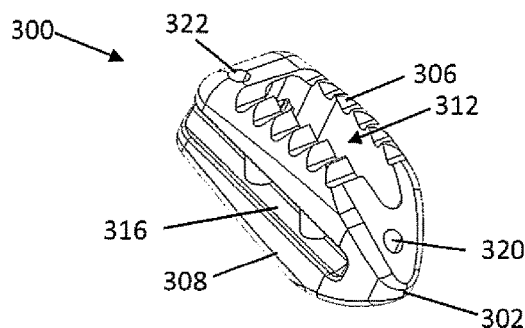
FIGS. 31 and 32 are perspective views of an example of an interbody implant suitable for use during the PLIF procedure of FIG. 1.
Figure 32:
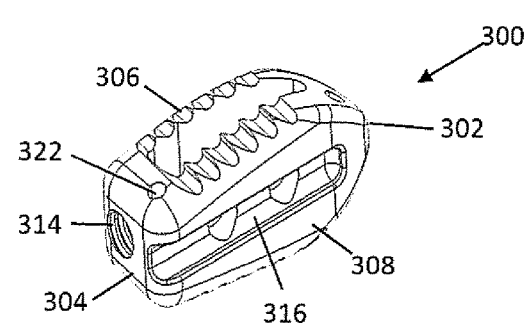
Figure 33:
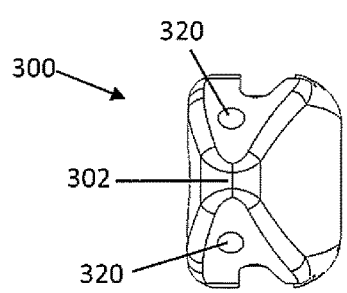
FIGS. 33 and 34 are plan views of the leading and trailing ends, respectively, of the interbody implant of FIG. 31.
Figure 34:
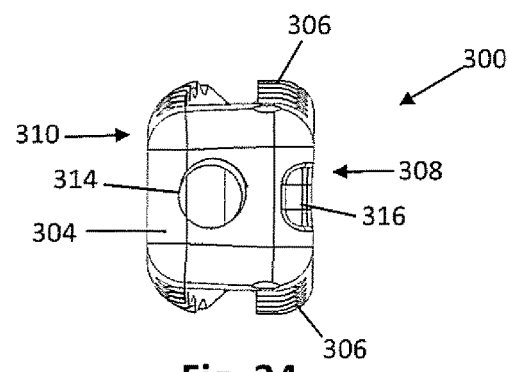
Figure 35:
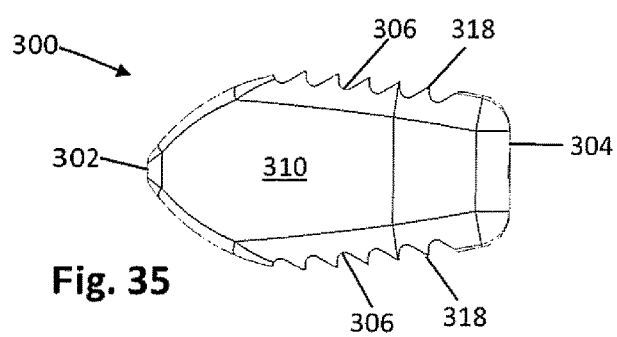
FIGS. 35 and 36 are plan views of the lateral sides of the interbody implant of FIG. 31.
Figure 36:
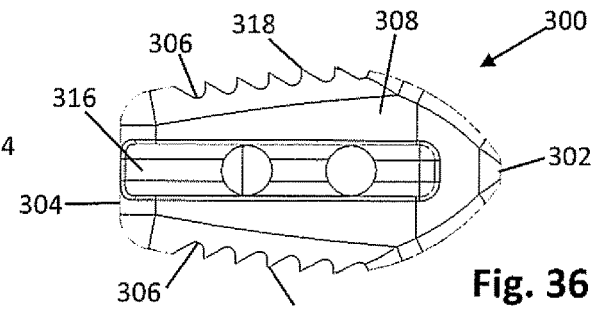
Figure 37:
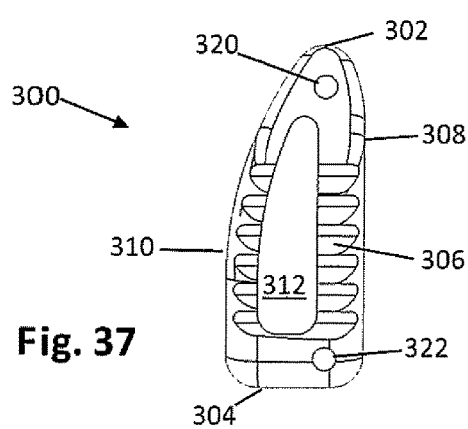
FIGS. 37 and 38 are plan views of the vertebral engaging sides of the interbody implant of FIG. 31.
Figure 38:
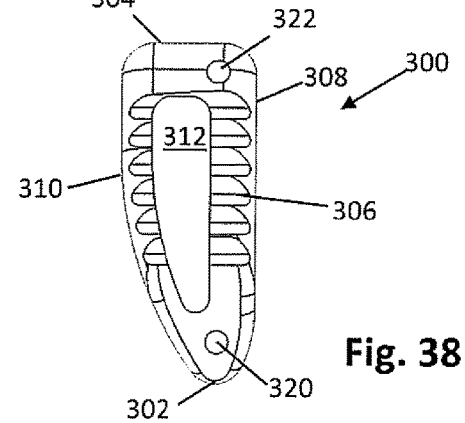

FIGS. 28-30 illustrate an example of a bone anchor 282 configured for use with the tissue retractor 10 during a medialized PLIF procedure according to one embodiment. By way of example only, the bone anchor 282 includes a tulip 284 and a shank 286. The tulip 284 is configured to lockingly receive a spinal rod 16 (FIG. 1) therein. The shank 286 includes a head 288, a neck 290, and a threaded region 292. The head 288 and neck 290 are configured to allow for polyaxial movement of the shank 286 relative to the tulip 284. By way of example only, the shank 286 comprises three different thread zones. The first thread zone 294 is configured to provide strong purchase in cortical bone. Cortical bone is prevalent at the posterior margin of the pedicle and is especially dense in the area surrounding the articulating surfaces of the facet where thread zone one will reside when fully inserted. The second thread zone 296 is configured to provide strong purchase through the pedicle where the cortical bone is less dense than the outer periphery cortical bone. The third thread zone 298 is configured to provide strong purchase in cortical bone. Cortical bone is prevalent at the anterio-lateral margin of the vertebral body within the ring apophysis in which the third thread zone 298 will reside when fully inserted. Third thread zone 298 is also configured to advance through the bone without creating voids within bone that would potentially reduce purchase of the first and/or second thread zones 294, 296, respectively. This is accomplished by providing a taper on the distal tip of the shank and on the second lead such that the second lead does not violate the minor diameter of the second thread zone 296 or the first thread zone 294.

FIGS. 31-38 illustrate an example of an interbody implant 300 configured for use with the tissue retractor 10 during a medialized PLIF procedure according to one embodiment. The interbody implant 300 includes a leading end 302, a trailing end 304, a pair of opposing vertebral contact surfaces 306, a first side 308, a second side 310, and a fusion aperture 312. The leading end 302 is tapered such that the implant 300 is capable of being impacted into an intervertebral disc space. The trailing end 304 includes an aperture 314 configured to engage an insertion tool (not shown). By way of example only, the aperture 314 is threaded, however other configurations are possible. The first side 308 includes an elongated recess 316 extending substantially the length of the first side 308 and intersecting with the trailing end 304. The elongated recess 316 is dimensioned to receive a stability prong of an insertion tool (not shown). The implant is configured specifically for far lateral positioning within the disc space. For example, the second side 310 is contoured to complement the lateral aspects of a vertebral body such that the implant may be positioned along the lateral edge and rests upon the dense cortical bone of the apophyseal ring along the lateral edge. As pictured in FIG. 47, an implant 300 is preferably positioned far laterally on each side of the disc space (e.g. bilaterally). This bilateral placement along the apophyseal ring on each lateral edge of the disc space provides structural advantage over typical bilateral PLIF implant positioning which does not extend out all the way to the lateral edges. The opposing contact surfaces 306 are configured such that either surface can be oriented to contact the upper vertebral body. Thus the implant 300 is reversible, or in other words, a single implant configuration can be utilized as either the left implant or right implant (when positioned bilaterally as preferred).

The implant 300 is configured to be inserted via straight impaction or an insert and rotate technique in which the implant is inserted on its side and then rotated into position inside the intervertebral space. To facilitate the insert and rotate technique for example, the first and second sides 308, 310 include smooth surfaces that taper toward the leading end 302. This allows for easier insertion into the disc space. The vertebral contact surfaces 306 may include anti-migration features 318 to prevent the implant 300 from migrating once it is positioned in the desired place in the intervertebral space. That is, the implant 300 is inserted with the first and second sides 308, 310 initially in contact with the vertebral endplates during insertion. Thereafter, the implant 300 is rotated 90° such that the vertebral contact surfaces 306 and specifically the anti-migration features 318 are brought into contact with the endplates. In this second orientation the implant 300 is also taller near the leading end 302 in order to accommodate the lordotic curvature of the lumbar spine. The fusion aperture 312 extends through the implant 300 between the vertebral contact surfaces 306 and is configured to receive fusion-promoting material. The implant 300 also includes a first radiographic marker 320 positioned near the leading end 302 and a second radiographic marker 322 positioned near the trailing end 304. The radiographic markers 320, 322 may be composed of any material suitable for viewing under fluoroscopy, for example including but not limited to titanium and other metals.

Traditional PLIF exposure requires exposure out to transverse process. Exposure includes stripping of musculature and associated morbidity. Screws are advanced into the vertebral body through the pedicle starting at the intersection of the transverse process and the inferior articulating process of the superior facet. Typical trajectories between pedicle screws within the same vertebral body converge. The trajectory is also often directed inferiorly.

The present application describes a medialized PLIF exposure. The medialized exposure can be made much smaller than the traditional exposure. Exposure does not require stripping of musculature all the way out to the transverse process. Exposure generally opens out only to the facet joints on the lateral margin. Screws are still advanced into the vertebral body through the pedicle, however, the starting point is more medial and slightly inferior. The starting point is typically just medial and inferior to the articulating surface of the superior facet.

Figure 39:
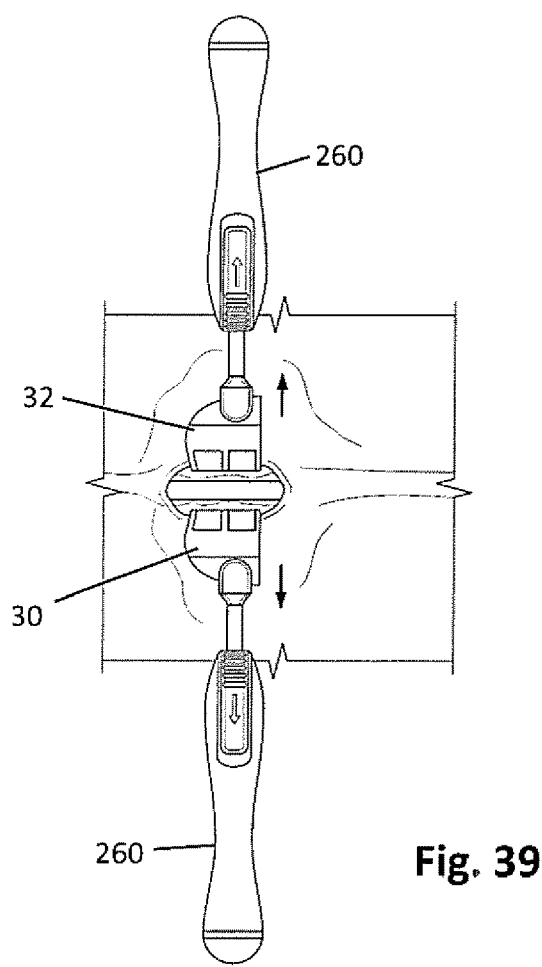
Figure 40:
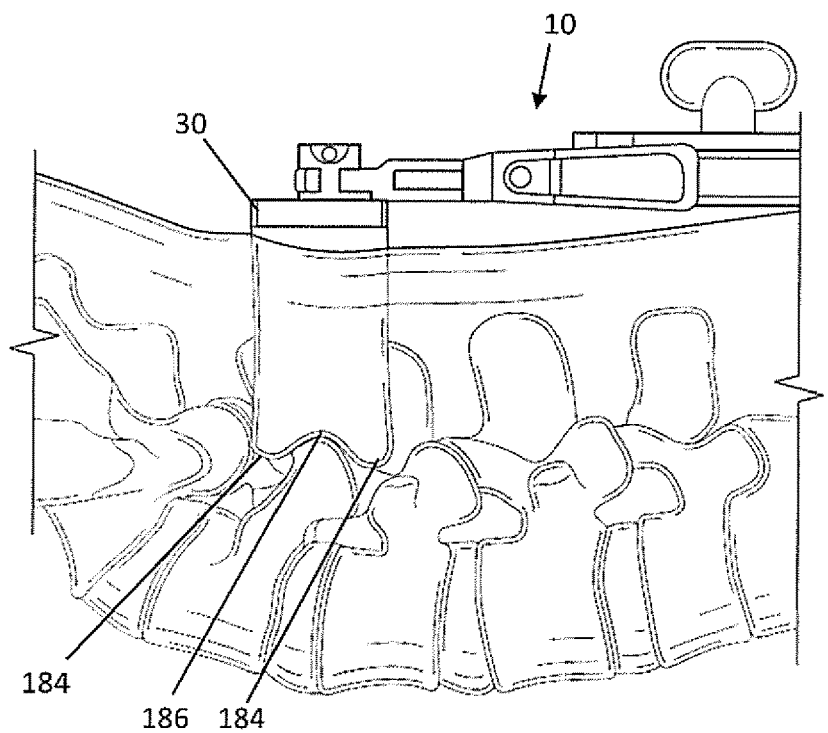
Figure 45:
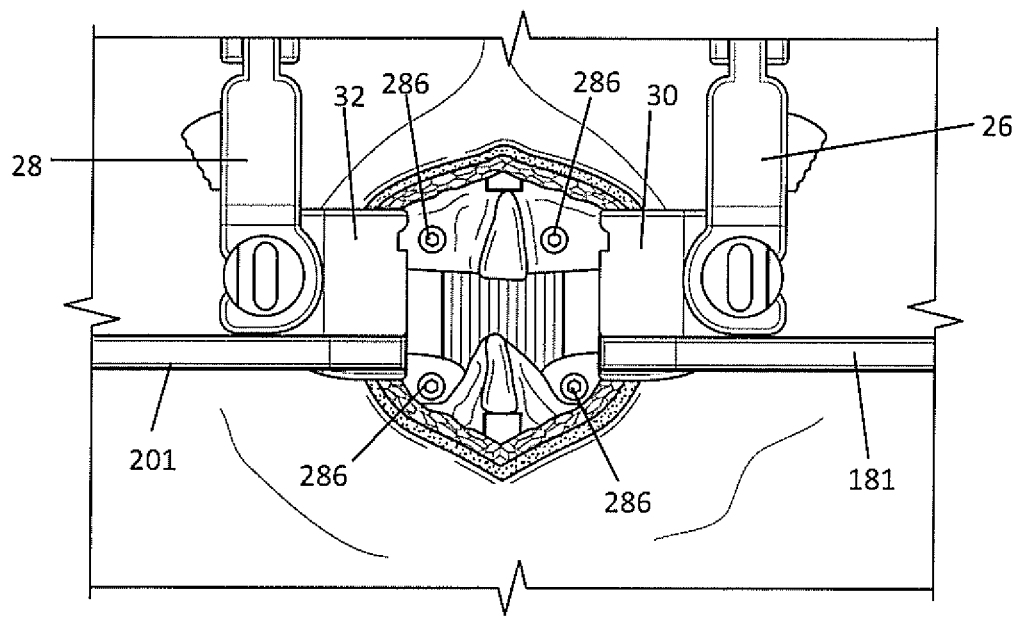

FIGS. 39-48 illustrate various steps in the method of performing a minimally invasive PLIF procedure using the tissue retractor 10, bone anchors 282, and implants 300, described herein according to one example embodiment. Referring first to FIG. 39, after the affected spinal level is identified, an incision is made exposing the spinal elements. The narrow retractor blade 228 is used first (both right and left blades. The narrow retractor blades are attached to the attachment handles 260 in the manner described above. The narrow retractor blades 228 may be used to retract the patient's tissue only until the blades are positioned directly over the facet capsule, with the center recess 244 resting on the facet bone (for example as shown in FIG. 40). In this manner the left and right retractor blades not only hold tissue out of the operative corridor but they also geographically define the exposure such that the blades essentially provide anatomy landmarks easily orienting the surgeon to anatomy within the exposure. While manually holding the exposure using the attachment handles 260, the right and left arms 26, 28 of the tissue retractor 10 may be attached to the right and left blades in the manner described above. The tissue retractor 10 is oriented so the access driver body 20 is placed cephalad of the exposure (FIG. 40). At this point, the tissue retractor 10 may be attached to an articulating arm in order to immobilize the retractor 10 relative to the operating table. Once the tissue retractor 10 has been attached to the articulating arm, the narrow retractor blades 228 may be replaced with the right and left wide retractor blades 30, 32 as desired. Alternatively, the right and left wide retractor blades 30, 32 may be used from the beginning of the procedure, or alternatively still the narrow retractor blades 228 may be used throughout the entire procedure. Light cables 181 may be introduced into the exposure by engaging the light guides 180 as described above.

The next step is to identify the proper trajectory for the bone anchors 12. FIGS. 41-44 illustrate the proper placement and trajectory of the bone anchors 12. FIG. 41 illustrates a spinal column with typical medialized trajectories $T_1$-$T_4$ as they are on multiple vertebral levels. Typical trajectories between medialized pedicle screws within the same vertebral body diverge and are also often directed slightly superiorly. Inserting screws along this trajectory generally allows for placement of a shorter screw shank than those placed along traditional PLIF trajectories because the medialized trajectory takes advantage of the anatomical location of cortical bone within the vertebral body. Cortical bone provides greater purchase to screws because it has a higher density as compared to cancellous bone. FIGS. 43-44 illustrate an example of three different spots 1, 2, 3 where the medialized trajectory $T_1$ takes advantage of the cortical bone. The cortical bone is located about the periphery of the vertebral body 3 and the periphery of the posterior elements including the pedicle 2. Once the proper location and trajectory has been determined, pilot holes $P_1$-$P_3$ (FIG. 42) are formed in the bone and the bone anchors 12 may be implanted. According to one example embodiment (and illustrated in FIG. 45), the shanks 286 may be implanted first and then the tulips 284 may be subsequently added near the end of the procedure. This allows for more space within the surgical exposure to operate on the spine (e.g. removing bone and disc material, positioning implants, etc. . . . ) as there is less hardware present during the procedure.

Figure 46:
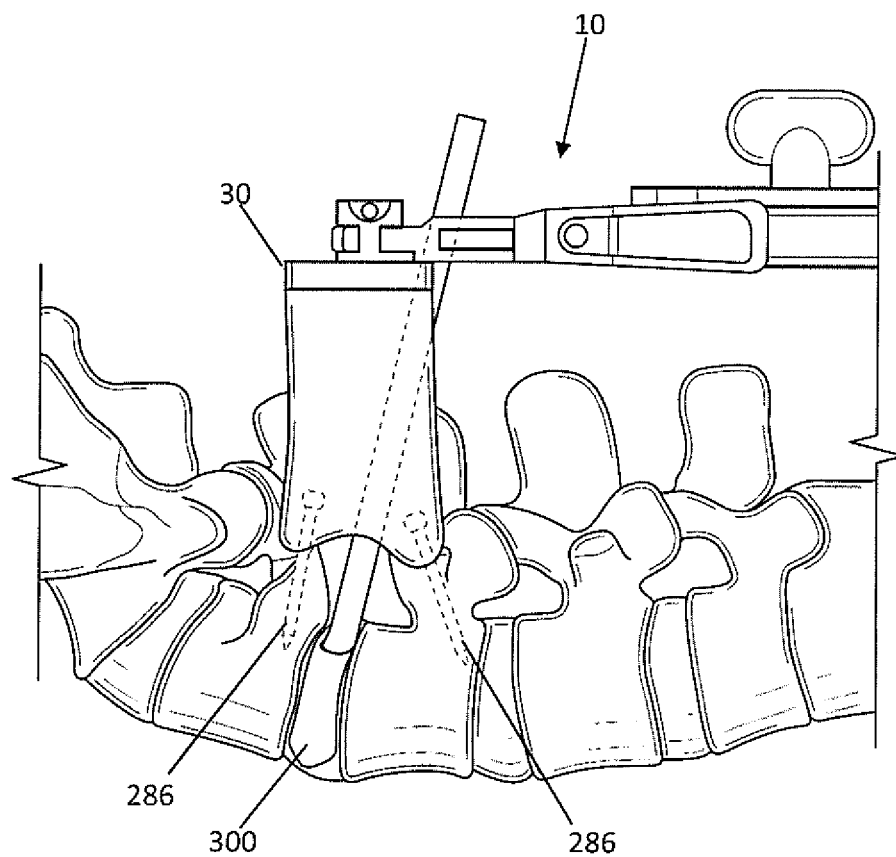
Figure 47:
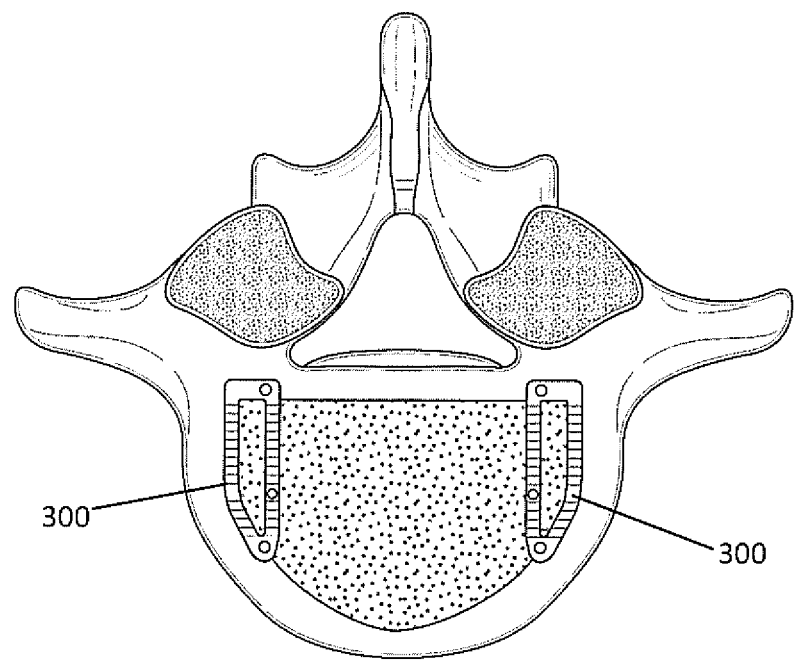
Figure 48:
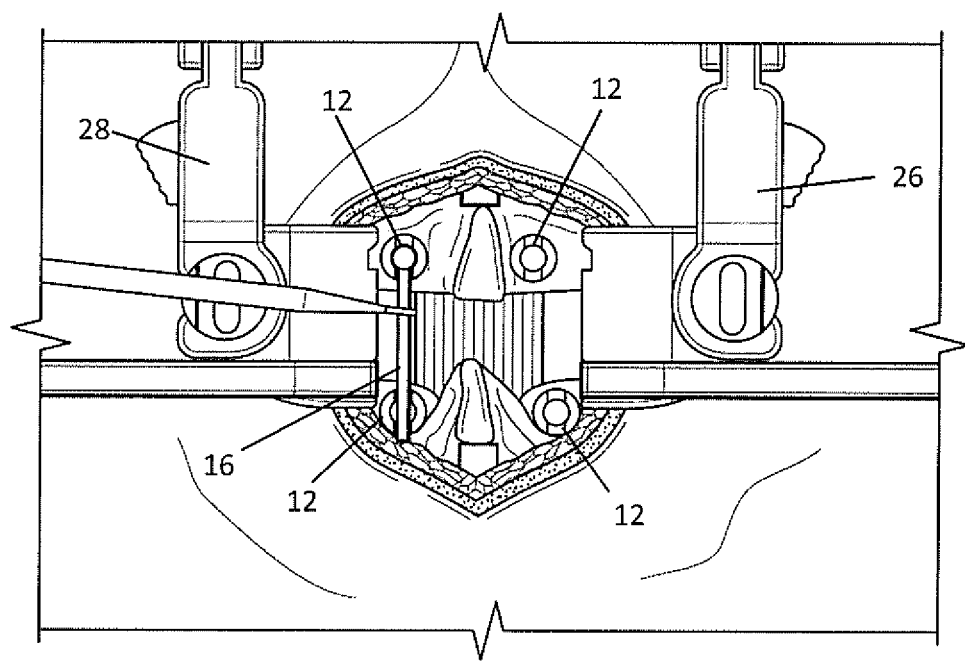

Once the shanks 286 have been implanted, the surgeon may perform a bilateral decompression by removing the inferior articular processes and superior ⅔ of the superior articular processes. A discectomy may then be performed in a conventional manner. After determining the appropriate sized interbody implants 300, the implants 300 are inserted into the disc space in the manner described above, using the insert and rotate technique (FIG. 46). By way of example, two interbody implants 300 may be implanted in the disc space, one on the contralateral side and one on the ipsilateral side. Proper placement of the implants 300 is shown in FIG. 47. Once the implants 300 are properly inserted, the tulips 284 may be added to the shanks 286 and the spinal rods 16 may be added, completing the construct (FIG. 48).

While the inventive features described herein have been described in terms of a preferred embodiment for achieving the objectives, it will be appreciated by those skilled in the art that variations may be accomplished in view of these teachings without deviating from the spirit or scope of the invention.

What is claimed is:

1. A surgical tissue retractor, comprising:
    a retractor body having:
        a first arm configured to couple with a first retractor blade; and
        a second arm configured to couple with a second retractor blade,
    wherein the retractor body is operable to adjust the spacing between the first retractor blade and second retractor blade;
    wherein the first retractor blade includes:
        a first connector being configured to couple with the first arm; and
        a first blade portion including:
            a first distal end;
            a first proximal end;
            a first maximum width; and
            a first longitudinal axis extending through the first proximal end and first distal end and passing through a midpoint of the first maximum width,
    wherein the first distal end has a first outer lobe situated on one side of the first longitudinal axis and a second outer lobe situated on the opposite side of the first longitudinal axis;
    wherein the first outer lobe and second outer lobe are separated by a first recess therebetween;
    wherein the second retractor blade includes:
        a second connector being configured to couple with the second arm; and
        a second blade portion including:
            a second distal end;
            a second proximal end;
            a second maximum width; and
            a second longitudinal axis extending through the second proximal end and second distal end and passing through a midpoint of the second maximum width;
    wherein the second distal end has a third outer lobe situated on one side of the second longitudinal axis and a fourth outer lobe situated on the opposite side of the second longitudinal axis;
    wherein the third outer lobe and fourth outer lobe are separated by a second recess therebetween;
    wherein the first arm includes a first blade receptacle configured to receive the first connector and the second arm includes a second blade receptacle configured to receive the second connector;
    wherein the first arm includes a first blade release mechanism associated with the first blade receptacle and the second arm includes a second blade release mechanism associated with the second blade receptacle; and
    wherein the first blade receptacle is partially spherical and open on one side.

2. The surgical tissue retractor of claim 1, wherein the first blade portion is asymmetric about the first longitudinal axis.

3. The surgical tissue retractor of claim 2, wherein the second blade portion is asymmetric about the second longitudinal axis.

4. The surgical tissue retractor of claim 1, wherein the first retractor blade can freely rotate within the first blade receptacle so as to self-align against tissue.

5. The surgical tissue retractor of claim 1, wherein the first connector of the first retractor blade is configured to be in coupled engagement with the first blade receptacle and a separate insertion tool at the same time.

6. The surgical tissue retractor of claim 5, wherein the first connector includes a connection head that is releasably engageable with an insertion tool and a connection post that is positionable within the first blade receptacle, the connection head having an outer circumference that is larger than the first blade receptacle.

7. The surgical tissue retractor of claim 1, wherein the first distal end and the second distal end are each toothed.

8. The surgical tissue retractor of claim 1, wherein the first arm is coupled to a first elongate support arm and the second arm is coupled to a second elongate support arm.

9. The surgical tissue retractor of claim 8, wherein the first elongate support arm and the second elongate support arm translate linearly relative to each other to adjust the spacing between the first retractor blade and second retractor blade.

10. The surgical retractor of claim 9, wherein the first elongate support arm and the second elongate support arm are situated parallel to each other.

11. The surgical tissue retractor of claim 10, wherein the first elongate support arm and the second elongate support arm are connected via an access driver, the access driver including a housing configured to receive the first and second elongate support arms, a pinion positioned between the first and second elongate support arms and simultaneously engaged with toothed sides of each of the first and second elongate support arms, the pinion being operable to cause translation of the first and second elongate support arms, and a pawl operable to prohibit translation of the first and second elongate support arms.

12. A surgical tissue retractor, comprising:
    a retractor body having:
        a first arm coupled to a first elongate support arm and being configured to couple with a first retractor blade; and a second arm coupled to a second elongate support arm and being configured to couple with a second retractor blade,
wherein the retractor body is operable to adjust the spacing between the first retractor blade and second retractor blade;
wherein the first retractor blade includes:
a first connector being configured to couple with the first arm; and
a first blade portion including:
a first distal end;
a first proximal end;
a first maximum width; and
a first longitudinal axis extending through the first proximal end and first distal end and passing through a midpoint of the first maximum width,
wherein the first distal end has a first outer lobe situated on one side of the first longitudinal axis and a second outer lobe situated on the opposite side of the first longitudinal axis;
wherein the first outer lobe and second outer lobe are separated by a first recess therebetween;
wherein the second retractor blade includes:
a second connector being configured to couple with the second arm; and
a second blade portion including:
a second distal end;
a second proximal end;
a second maximum width; and
a second longitudinal axis extending through the second proximal end and second distal end and passing through a midpoint of the second maximum width;
wherein the second distal end has a third outer lobe situated on one side of the second longitudinal axis and a fourth outer lobe situated on the opposite side of the second longitudinal axis; and
wherein the third outer lobe and fourth outer lobe are separated by a second recess therebetween.

13. The surgical tissue retractor of claim 12, wherein the first arm includes a first blade receptacle configured to receive the first connector and the second arm includes a second blade receptacle configured to receive the second blade connector.

14. The surgical tissue retractor of claim 13, wherein the first arm includes a first blade release mechanism associated with the first blade receptacle and the second arm includes a second blade release mechanism associated with the second blade receptacle.

15. The surgical tissue retractor of claim 14, wherein the first blade receptacle is open on one side.

16. The surgical tissue retractor of claim 15, wherein the first blade release mechanism includes an engagement latch and a release button.

17. The surgical tissue retractor of claim 16, wherein the engagement latch includes a blocking element, an engagement arm that extends away from the blocking element, and a pivot point between the blocking element and the engagement arm, the blocking element being biased to a resting position in which the blocking element extends into the first blade receptacle.

18. The surgical tissue retractor of claim 17, wherein the release button includes a button end, a release arm extending from the button end and a pivot point between the button end and the release arm, the button end being biased to a resting position in which the button end extends laterally from a recess in the first arm.

19. The surgical tissue retractor of claim 18, wherein the engagement arm and the release arm are in contact with each other when the blocking element and button end are in the resting position.

20. The surgical tissue retractor of claim 12, wherein the first elongate support arm and the second elongate support arm translate linearly relative to each other to adjust the spacing between the first retractor blade and second retractor blade.

21. The surgical retractor of claim 20, wherein the first elongate support arm and the second elongate support arm are situated parallel to each other.

22. The surgical tissue retractor of claim 21, wherein the first elongate support arm and the second elongate support arm are connected via an access driver, the access driver including a housing configured to receive the first and second elongate support arms, a pinion positioned between the first and second elongate support arms and simultaneously engaged with toothed sides of each of the first and second elongate support arms, the pinion being operable to cause translation of the first and second elongate support arms, and a pawl operable to prohibit translation of the first and second elongate support arms.

23. A surgical tissue retractor, comprising:
a retractor body having:
a first arm configured to couple with a first retractor blade; and
a second arm configured to couple with a second retractor blade,
wherein the retractor body is operable to adjust the spacing between the first retractor blade and second retractor blade;
wherein the first retractor blade includes:
a first connector being configured to couple with a blade receptacle of the first arm and a separate insertion tool at a same time; and
a first blade portion including:
a first distal end;
a first proximal end;
a first maximum width; and
a first longitudinal axis extending through the first proximal end and first distal end and passing through a midpoint of the first maximum width,
wherein the first distal end has a first outer lobe situated on one side of the first longitudinal axis and a second outer lobe situated on the opposite side of the first longitudinal axis;
wherein the first outer lobe and second outer lobe are separated by a first recess therebetween;
wherein the second retractor blade includes:
a second connector being configured to couple with the second arm; and
a second blade portion including:
a second distal end;
a second proximal end;
a second maximum width; and
a second longitudinal axis extending through the second proximal end and second distal end and passing through a midpoint of the second maximum width;
wherein the second distal end has a third outer lobe situated on one side of the second longitudinal axis and a fourth outer lobe situated on the opposite side of the second longitudinal axis;
wherein the third outer lobe and fourth outer lobe are separated by a second recess therebetween.

24. The surgical tissue retractor of claim 23, wherein the first connector includes a connection head that is releasably engageable with an insertion tool and a connection post that is positionable within the blade receptacle, the connection head having an outer circumference that is larger than the blade receptacle.

* * * * *